(12) United States Patent
Kurosaki et al.

(10) Patent No.: US 11,446,475 B2
(45) Date of Patent: Sep. 20, 2022

(54) BALLOON CATHETER, METHOD OF MANUFACTURING A BALLOON CATHETER, AND TREATMENT METHOD

(71) Applicant: TERUMO KABUSHIKI KAISHA, Tokyo (JP)

(72) Inventors: Yasuo Kurosaki, Kanagawa (JP); Katsumi Morimoto, Kanagawa (JP); Hiroshi Goto, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 212 days.

(21) Appl. No.: 16/127,586

(22) Filed: Sep. 11, 2018

(65) Prior Publication Data

US 2019/0009065 A1     Jan. 10, 2019

Related U.S. Application Data

(63) Continuation of application No. PCT/JP2017/011635, filed on Mar. 23, 2017.

(30) Foreign Application Priority Data

Mar. 23, 2016   (JP) .............................. JP2016-058041

(51) Int. Cl.
  *A61M 25/10*   (2013.01)
  *A61L 29/16*   (2006.01)
  (Continued)

(52) U.S. Cl.
  CPC ....... *A61M 25/1029* (2013.01); *A61K 31/337* (2013.01); *A61K 31/436* (2013.01);
  (Continued)

(58) Field of Classification Search
  CPC .... A61M 2025/1086; A61M 2025/105; A61M 2025/1031; A61M 2025/1004;
  (Continued)

(56) References Cited

U.S. PATENT DOCUMENTS

2009/0240270 A1   9/2009  Schneider et al.
2009/0246252 A1 * 10/2009  Arps ..................... A61L 29/041
                                                         424/425
(Continued)

FOREIGN PATENT DOCUMENTS

JP    2011-515147 A    5/2011
JP    2012-502690 A    2/2012
WO    2015/151876 A1  10/2015

OTHER PUBLICATIONS

International Search Report (PCT/ISA/210) dated Jun. 20, 2017, by the Japanese Patent Office as the International Searching Authority for International Application No. PCT/JP2017/011635.

(Continued)

*Primary Examiner* — Rebecca E Eisenberg
*Assistant Examiner* — Anna E Goldberg-Richmeier
(74) *Attorney, Agent, or Firm* — Buchanan Ingersoll & Rooney PC

(57) ABSTRACT

A balloon catheter by which a drug can be effectively delivered to living body tissue and a method of manufacturing the balloon catheter, and a treatment method. The balloon catheter is provided on an outer surface of a balloon with a plurality of elongate bodies which are independent crystals of a water-insoluble drug that extend in an elongate form. The elongate bodies have long axes extending in directions along the outer surface of the balloon when the balloon is in a deflated state. Deformation, when the balloon is inflated from the deflated state, of portions on an outer surface side of the balloon to which end portions of the elongate bodies are fixed causes a force to act on the elongate bodies such that the long axes of the elongate bodies approach perpendicularity to the outer surface of the balloon.

17 Claims, 15 Drawing Sheets

(51) Int. Cl.
*A61K 31/436* (2006.01)
*A61K 31/337* (2006.01)

(52) U.S. Cl.
CPC ............. *A61L 29/16* (2013.01); *A61M 25/10* (2013.01); *A61L 2300/416* (2013.01); *A61L 2300/426* (2013.01); *A61M 2025/105* (2013.01); *A61M 2025/1031* (2013.01); *A61M 2025/1086* (2013.01)

(58) Field of Classification Search
CPC .. A61M 2025/1081; A61M 2025/0023; A61M 2025/0057; A61M 2025/1075; A61M 25/10; A61M 25/1029; A61M 25/0045; A61M 25/104
See application file for complete search history.

(56) References Cited

U.S. PATENT DOCUMENTS

| | | | | |
|---|---|---|---|---|
| 2009/0258049 | A1* | 10/2009 | Klein | A61L 29/10 514/277 |
| 2010/0042121 | A1* | 2/2010 | Schneider | A61B 17/205 606/159 |
| 2010/0069879 | A1 | 3/2010 | Michal et al. | |
| 2012/0259405 | A1 | 10/2012 | Weber et al. | |
| 2013/0060189 | A1* | 3/2013 | Herman | A61M 25/0074 604/173 |
| 2013/0116655 | A1* | 5/2013 | Bacino | A61M 25/10184 604/509 |
| 2014/0271775 | A1* | 9/2014 | Cleek | A61L 27/54 427/2.25 |
| 2017/0014860 | A1 | 1/2017 | Kurosaki et al. | |

OTHER PUBLICATIONS

Written Opinion (PCT/ISA/237) dated Jun. 20, 2017, by the Japanese Patent Office as the International Searching Authority for International Application No. PCT/JP2017/011635.

English translation of the Written Opinion of the International Searching Authority and International Search Report dated Jun. 20, 2017 in International Application No. PCT/JP2017/011635.

The extended European Search Report dated Jul. 4, 2019, by the European Patent Office in corresponding European Patent Application No. 17770322.0-1132. (5 pages).

* cited by examiner

BALLOON CATHETER, METHOD OF MANUFACTURING A BALLOON CATHETER, AND TREATMENT METHOD

CROSS-REFERENCES TO RELATED APPLICATIONS

This application is a continuation of International Application No. PCT/JP2017/011635 filed on Mar. 23, 2017, which claims priority to Japanese Application No. 2016-058041 filed on Mar. 23, 2016, the entire contents of both of which is incorporated herein by reference.

TECHNICAL FIELD

The present disclosure relates to a balloon catheter having a balloon coated on its surface with a crystalline drug, a method of manufacturing a balloon catheter, and a treatment method using the balloon catheter.

BACKGROUND ART

In recent years, for improving lesion affected areas (stenosed parts) in body lumens, balloon catheters have been used. A balloon catheter normally includes an elongate shaft section, and a balloon which is provided on the distal side of the shaft section and is inflatable in the radial direction. After the balloon in a deflated state is brought to a target site in the body by way of a thin body lumen, the balloon is inflated, whereby the lesion affected area can be pushed wide open (widened).

However, if a lesion affected area is forcibly pushed wide open, excessive proliferation of smooth muscle cells may occur, causing new stenosis (restenosis) at the lesion affected area. In view of this, recently, drug eluting balloons (DEBs) in which an outer surface of a balloon is coated with a drug for restraining stenosis have been used. The drug eluting balloon, by being inflated, is able to instantaneously release the drug contained in the coating on the outer surface of the balloon to the lesion affected area, thereby restraining restenosis.

In recent years, it has been becoming clear that the morphological form of the drug in the coating on the surface of the balloon influences the releasing property of the drug from the balloon surface and/or the tissue transferability of the drug at the lesion affected area. For instance, U.S. Patent Application Publication No. 2014/0271775 describes a balloon catheter in which crystals of a drug are formed in elongate form on a surface of a balloon.

SUMMARY

For enhancing a therapeutic effect, a drug eluting balloon catheter is desirably configured in such a manner that the deliverability of the drug on the surface of the balloon to living body tissue is relatively high.

A balloon catheter is disclosed by which a drug can be effectively delivered to living body tissue and a method of manufacturing a balloon catheter, and a treatment method.

A balloon catheter according to the present disclosure for achieving the aforesaid objects is a balloon catheter provided on an outer surface of a balloon with a plurality of elongate bodies which are crystals of a water-insoluble drug that extend while having independent long axes. The elongate bodies have the long axes (i.e., longitudinal axis) extending in directions along the outer surface of the balloon when the balloon is in a deflated state, and deformation, when the balloon is inflated from the deflated state, of portions on an outer surface side of the balloon to which end portions of the elongate bodies are fixed (held or attached) causes a force to act on the elongate bodies such that the long axes of the elongate bodies approach perpendicularity to the outer surface of the balloon.

In the balloon catheter configured as aforesaid, inflation of the balloon causes the long axes of the elongate bodies approach perpendicularity to the outer surface of the balloon, so that the elongate bodies become liable (i.e., likely) to pierce the living body tissue. As a result, releasing property (i.e., ability of the drug to be released) of the drug from the outer surface of the balloon and transferability of the drug (i.e., the transferability of the drug onto the tissue) to the living body tissue can be enhanced, and the drug can be effectively delivered to the living body tissue. Note that the portions on the outer surface side of the balloon are not limited to the portions constituted of the balloon itself, and may be portions (for example, a layer of an excipient) formed on the outer surface of the balloon.

The balloon may have an overlapping portion where portions of the outer surface of the balloon overlap with each other when the balloon is folded in the deflated state, and the elongate bodies may be provided on the portions of the outer surface of the balloon that overlap with each other at the overlapping portion, which helps ensure that the elongate bodies are not exposed to the outside when the balloon is in the deflated state, so that the elongate bodies can be protected until the balloon reaches the target position. Therefore, the drug can be restrained (or prevented) from falling off (i.e., be removed from) the outer surface of the balloon or flowing out into blood stream or the like during delivery, and the drug can be effectively delivered to the living body tissue.

The water-insoluble drug may be rapamycin, paclitaxel, docetaxel, or everolimus. As a result of this, restenosis at a stenosed part in a blood vessel can be favorably restrained by the elongate bodies.

In addition, a method of manufacturing a balloon catheter according to the present disclosure is a method of manufacturing a balloon catheter provided on an outer surface of a balloon with a plurality of elongate bodies which are crystals of a water-insoluble drug that extend while having independent long axes, the method including a step of forming the elongate bodies on the outer surface of the balloon, a step of forming the balloon with a wing portion projecting in a radial direction, and a step of folding the wing portion, formed in the balloon, along a circumferential direction. In at least one of the step of forming the wing portion and the step of folding the wing portion, portions on an outer surface side of the balloon to which end portions of the elongate bodies are fixed are deformed by a force exerted for deforming the balloon, whereby the long axes of the elongate bodies are inclined into directions along the outer surface of the balloon. According to the method of manufacturing a balloon catheter configured as aforesaid, the elongate bodies fixed to the portions on the outer surface side of the balloon can be efficiently inclined, through utilization of the force exerted on the balloon in the step of forming the balloon with the wing portion or the step of folding the wing portion.

An overlapping portion where portions of the outer surface of the balloon overlap with each other may be formed, in the step of folding the wing portion, and the long axes of the elongate bodies provided on the portions of the outer surface that face each other at the overlapping portion may be inclined into directions along the outer surface of the balloon, which helps ensure that the force exerted on the balloon for folding the wing portion acts on the surfaces located inside the overlapping portion indirectly, so that the force acting on the elongate bodies can be controlled, and a desirable force for inclining the elongate bodies can be easily exerted.

In addition, a treatment method according to the present disclosure is a treatment method of delivering a drug to a lesion affected area in a body lumen by use of the aforementioned balloon catheter, the treatment method including a step of inserting the balloon into the body lumen to deliver the balloon to the lesion affected area, a step of inflating the balloon to cause the elongate bodies to be erected at such an angle as to approach perpendicularity to the outer surface of the balloon, a step of pressing the erected elongate bodies against living body tissue, and a step of deflating the balloon and withdrawing the balloon out of the body lumen. In the treatment method configured as aforesaid, inflation of the balloon causes the long axes of the elongate bodies which are crystals of a water-insoluble drug to approach perpendicularity to the outer surface of the balloon, so that the elongate bodies become liable (i.e., likely) to pierce the living body tissue. As a result, releasing property of the drug from the outer surface of the balloon and transferability of the drug to the living body tissue can be relatively enhanced, and the drug can be effectively delivered to the living body tissue.

BRIEF DESCRIPTION OF THE DRAWINGS

FIGS. 18A-18C are sectional views depicting a balloon folded by the balloon folding apparatus, in which FIG. 18A depicts a state before folding of the balloon, FIG. 18B depicts a state in which the wing portions are formed by the pleating section, and FIG. 18C depicts a state in which the wing portions are folded by the folding section.

DETAILED DESCRIPTION

Figure 1:
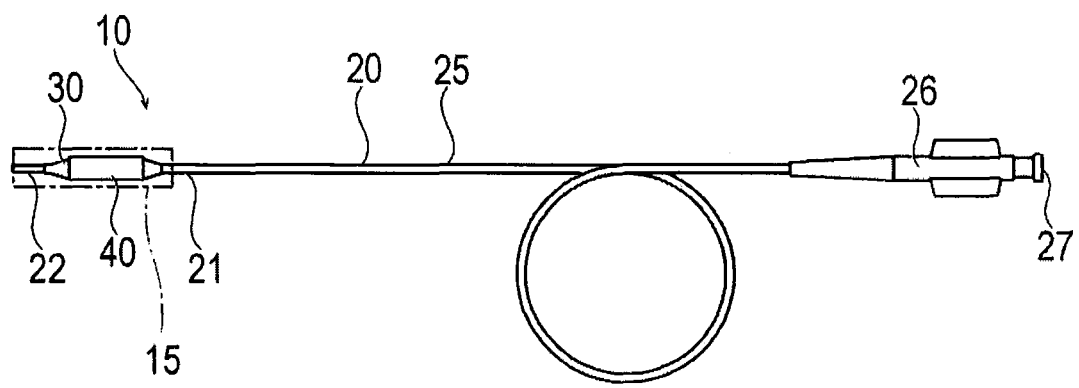
FIG. 1 is a front view of a balloon catheter according to the present embodiment.

An embodiment of the present disclosure will be described below referring to the drawings. Note that the dimensional ratios in the drawings may be exaggerated and different from the actual ratios, for convenience of explanation.

Figure 2:
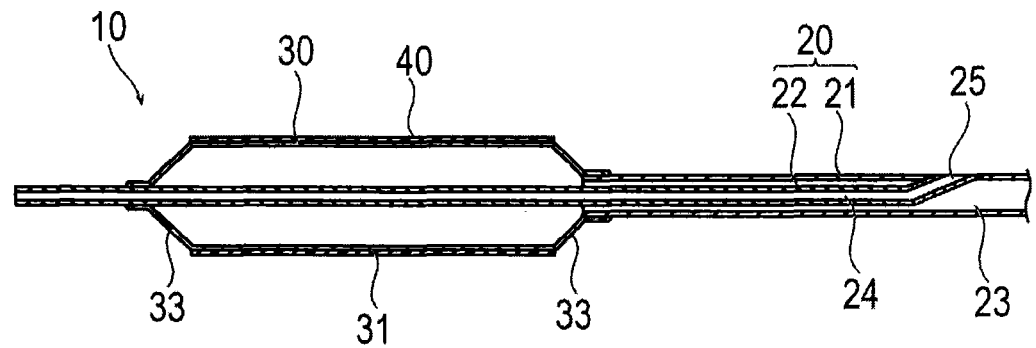
FIG. 2 is a sectional view of a distal portion of the balloon catheter.

As depicted in FIGS. 1 and 2, a balloon catheter 10 according to an embodiment of the present disclosure is a drug eluting type catheter provided with crystals of a drug on an outer surface of a balloon 30. Note that, in the present specification, the side on which the balloon catheter 10 is inserted into a body lumen will be referred to as "distal end" or "distal side," while the operator's hand side on which the balloon catheter 10 is operated will be referred to as "proximal end" or "proximal side."

First, the structure of the balloon catheter 10 will be described. The balloon catheter 10 includes an elongate catheter main body 20, the balloon 30 provided at a distal portion of the catheter main body 20, a coating layer 40 that contains a drug and that is provided on the outer surface of the balloon 30, and a hub 26 firmly attached to a proximal end of the catheter main body 20. The balloon 30 provided with the coating layer 40 is protected by being covered with a protective sheath 15 until put to use.

The catheter main body 20 includes an outer tube 21 that is a tube body opening at a distal end and a proximal end, and an inner tube 22 that is a tube body disposed inside the outer tube 21. The inner tube 22 is accommodated in the hollow (i.e., an annular space or lumen) inside of the outer tube 21, and the catheter main body 20 has a double-tube structure at a distal portion of the catheter main body 20. The hollow inside of the inner tube 22 is a guide wire lumen 24 for passing a guide wire therethrough (i.e., a guide wire is positionable in or insertable through the guide wire lumen 24). In addition, in the hollow inside of the outer tube 21 and on the outside of the inner tube 22, there is formed an inflation lumen 23. An inflation fluid for inflating the balloon 30 may pass through the inflation lumen 23. The inner tube 22 is opening to the exterior (i.e., surrounding environment) at an opening portion 25. The inner tube 22 protrudes to the distal side beyond a distal end of the outer tube 21.

Of the balloon 30, a proximal-side end portion is fixed to a distal portion of the outer tube 21, and a distal-side end portion is fixed to a distal portion of the inner tube 22. This results in that the inside of the balloon 30 communicates with the inflation lumen 23. With the inflation fluid injected through the inflation lumen 23 into the balloon 30, the balloon 30 can be inflated. The inflation fluid may be a gas or a liquid; for example, gases such as helium gas, $CO_2$ gas, $O_2$ gas, $N_2$ gas, Ar gas, air, or mixed gas, and liquids such as physiological saline solution or a contrast agent, can be used as the inflation fluid.

At a central portion in regard of the axial direction of the balloon 30, there is formed a hollow cylindrical straight portion 31 (inflatable portion) having an equal outside diameter when inflated, and tapered portions 33 where the outside diameter gradually varies are formed on both sides of the straight portion 31 in regard of the axial direction. In addition, a coating layer 40 which contains a drug is formed on the whole part of the outer surface of the straight portion 31. Note that the range of the balloon 30 in which the coating layer 40 is formed is not limited only to the straight portion 31; the range may include at least part of the tapered portions 33 in addition to the straight portion 31, or may be only part of the straight portion 31.

The hub 26 is formed with a proximal opening portion 27 that communicates with the inflation lumen 23 of the outer tube 21 and that functions as a port for permitting the inflation fluid to flow in and out therethrough.

The length in an axial direction of the balloon 30 is not particularly limited, and is, for example, preferably 5 mm to 500 mm, more preferably 10 mm to 300 mm, and still more preferably 20 mm to 200 mm.

The outside diameter of the balloon 30 when inflated is not specifically restricted, and is, for example, preferably 1 mm to 10 mm, and more preferably 2 mm to 8 mm.

The outer surface of the balloon 30 before the formation of the coating layer 40 is smooth and non-porous. The outer surface of the balloon 30 before the formation of the coating layer 40 may have minute holes that do not pierce through the film. Alternatively, the outer surface of the balloon 30 before the formation of the coating layer 40 may have both a region of being smooth and non-porous and a region of having minute (i.e., extremely small) holes that do not pierce through the film. The minute holes may be sized to have, for example, a diameter of 0.1 µm to 5 µm and a depth of 0.1 µm to 10 µm, and one or a plurality of holes may be provided per drug crystal. In addition, the minute (i.e., extremely small) holes may be sized to have, for example, a diameter of 5 µm to 500 µm and a depth of 0.1 µm to 50 µm, and one or a plurality of drug crystals may be provided per one hole.

Preferably, the balloon 30 has a certain degree of flexibility and a certain degree of hardness such that the drug can be released from the coating layer 40 provided on the surface of the balloon 30 when the balloon 30 is inflated upon arrival at a blood vessel or tissue. Specifically, the balloon 30 is formed from metal or resin. It is preferable that at least the outer surface of the balloon 30 on which to provide the coating layer 40 is formed of resin. Examples of the material which can be used for forming at least the outer surface of the balloon 30 include thermoplastic resins such as polyolefins (e.g., polyethylene, polypropylene, polybutene, ethylene-propylene copolymers, ethylene-vinyl acetate copolymers, ionomers, or mixtures of two or more of them), flexible polyvinyl chloride resin, polyamides, polyamide elastomers, nylon elastomers, polyester, polyester elastomers, polyurethane, fluororesins, etc., silicone rubbers, and latex rubbers. Among the thermoplastic resins, preferred are the polyamides. Specifically, at least part of the outer surface of the inflatable portion of the balloon 30 to be coated with the drug is made of a polyamide. The polyamide is not particularly limited so long as it is a polymer which has an amide linkage. Examples of the polyamide include homopolymers such as polytetramethylene adipamide (nylon 46), polycaprolactam (nylon 6), polyhexamethylene adipamide (nylon 66), polyhexamethylene sebacamide (nylon 610), polyhexamethylene dodecamide (nylon 612), polyundecanolactam (nylon 11), polydodecanolactam (nylon 12), etc., copolymers such as caprolactam/lauryllactam copolymer (nylon 6/12), caprolactam/aminoundecanoic acid copolymer (nylon 6/11), caprolactam/ω-aminononanoic acid copolymer (nylon 6/9), caprolactam/hexamethylenediammonium adipate copolymer (nylon 6/66), etc., and aromatic polyamides such as copolymers of adipic acid with metaxylenediamine, or copolymers of hexamethylenediamine with m,p-phthalic acid. Further, polyamide elastomers as block copolymers in which nylon 6, nylon 66, nylon 11, nylon 12 or the like constitutes hard segments and a polyalkylene glycol, a polyether, an aliphatic polyester or the like constitutes soft segments can also be used as the base material of the medical device according to the present disclosure. One of the aforesaid polyamides may be used singly, or two or more of the aforesaid polyamides may be used in combination. Particularly, the balloon 30 preferably has a smooth surface of a polyamide.

Figure 3:
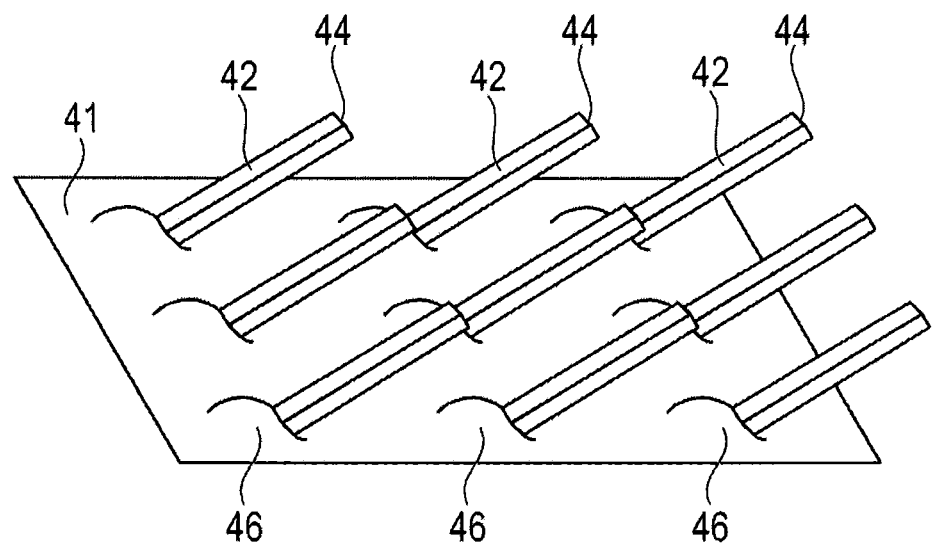
FIG. 3 is a schematic perspective view of elongate bodies composed of drug crystals on an outer surface of a balloon.
Figure 4:
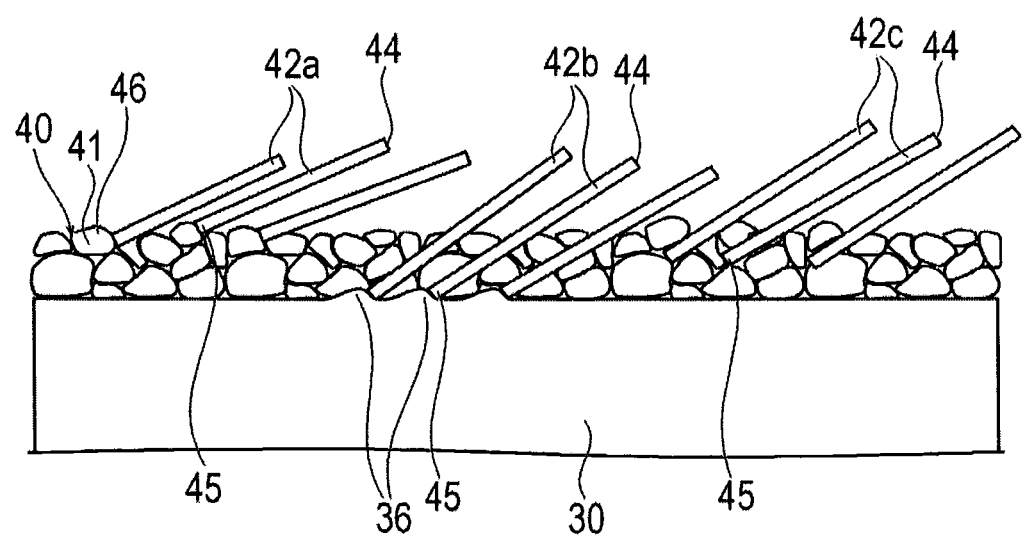
FIG. 4 is a schematic view of the elongate bodies composed of drug crystals and a base material, on the outer surface of the balloon.
Figure 5:
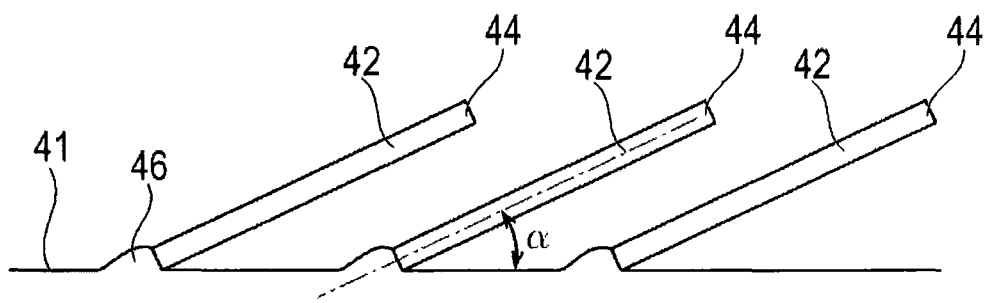
FIG. 5 is a front view of the elongate bodies provided on the outer surface of the balloon.

The balloon 30 is formed on an outer surface of the balloon 30 with the coating layer 40, either directly or through a pre-treatment layer such as a primer layer between the balloon 30 and the coating layer 40, by a method which will be described later. As depicted in FIGS. 3 to 5, the coating layer 40 includes a base material 41 (excipient) which is an additive layer containing a water-soluble low-molecular compound disposed in a layer form on the outer surface of the balloon 30, and a plurality of elongate bodies 42 which are crystals of a water-insoluble drug that extend while having independent long axes.

The elongate bodies 42 include first elongate bodies 42a that extend from the outer surface of the base material 41 toward the outside of the surface, second elongate bodies 42b that extend from the outer surface of the balloon 30 to the outside of the base material 41 by penetrating the base material 41, and third elongate bodies 42c that extend from the inside of the base material 41 to the outside of the base material 41. In other words, base portions 45 of the elongate bodies 42 may be in direct contact with the outer surface of the balloon 30, or may not make direct contact with the outer surface of the balloon 30 but the base material 41 (excipient) may be present between the base portions 45 and the outer surface of the balloon 30. Since the elongate bodies 42a, 42b and 42c are different in deliverability of the drug to the living body, it is possible, by regulating the positions of the base portions 45 of the crystals of the drug, to control the deliverability of the drug. Preparation may be made in which almost only the elongate bodies 42a are present on the surface of the balloon 30. Preparation may be made in which almost only the elongate bodies 42b are present on the surface of the balloon 30. Preparation may be made in which almost only the elongate bodies 42c are present on the surface of the balloon 30. In addition, preparation may be made in which a combination of the plurality of kinds of elongate bodies are present on the surface of the balloon 30. Examples of such a combination include a combination of the elongate bodies 42a with the elongate bodies 42b, a combination of the elongate bodies 42b with the elongate bodies 42c, and a combination of the elongate bodies 42c with the elongate bodies 42a. Preparation may be made in which all the elongate bodies 42a, 42b and 42c are present on the surface of the balloon 30.

In addition, a long axis of each of the elongate bodies 42 is inclined relative to the outer surface of the balloon 30, in a state in which the balloon 30 is deflated (a state before use). Therefore, the long axes of the elongate bodies 42 extend into directions along the outer surface of the balloon 30. When the first elongate bodies 42a and the third elongate bodies 42c, of which the base portions 45 are in contact not with the balloon 30 but with the base material 41, are inclined relative to the outer surface of the balloon 30 in the manufacturing process which will be described later, the base material 41 is deformed, whereby base material deformed portions 46 are formed. Attendant on the deformation of the base material 41, the outer surface of the balloon 30 may also be deformed. In the inside of the base material deformed portions 46, stress due to deformation may be left. The base material deformed portions 46 appear, for example, as projected portions or recessed portions in the outer surface of the base material 41. When the second elongate bodies 42b, of which the base portions 45 are in contact with the balloon 30, are inclined relative to the outer surface of the balloon 30 in the manufacturing process which will be described later, the balloon 30 is deformed, whereby balloon deformed portions 36 are formed. In the inside of the balloon deformed portions 36, stress due to deformation may be left. Further, the second elongate bodies 42b are penetrating the base material 41, and, therefore, the base material deformed portions 46 are also formed. The balloon deformed portions 36 appear, for example, as projected portions or recessed portions in the outer surface of the balloon 30.

The inclination angle α of the elongate bodies 42 relative to the outer surface of the balloon 30 or the base material 41 when the balloon 30 is in the deflated state is not particularly limited; as depicted in FIG. 5, the inclination angle α is, for example, preferably 0 degrees to 89 degrees, more preferably 3 degrees to 80 degrees, and still more preferably 30 degrees to 45 degrees.

Figure 6:
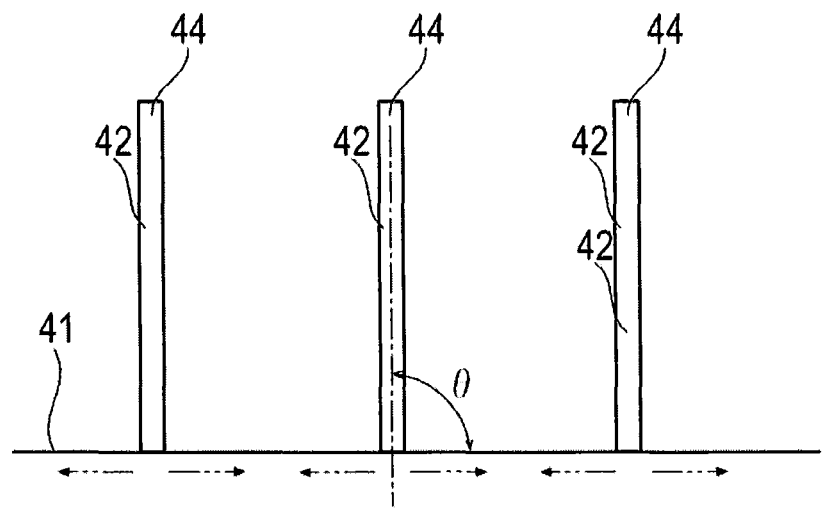
FIG. 6 is a front view depicting a state in which the elongate bodies provided on the outer surface of the balloon are erected.

When an inflation fluid is made to flow into the inside of the balloon 30 to inflate the balloon 30, the materials of the balloon 30 and the base material 41 are stretched in the circumferential direction, as depicted in FIG. 6 (see alternate long and two short dashes line in the figure). As a result, the balloon deformed portions 36 and the base material deformed portions 46 are stretched to return into original smooth shapes, and the long axes of the elongate bodies 42 approach perpendicularity to the outer surface of the balloon 30. The angle θ of the long axis of the elongate body 42 relative to the outer surface of the balloon 30 after inflation of the balloon 30 is greater than the angle α, preferably close to 90 degrees. The angle θ is, for example, 1 degree to 90 degrees, preferably 30 degrees to 90 degrees, more preferably 45 degrees to 90 degrees, and still more preferably 60 degrees to 90 degrees. Note that with the balloon 30 folded and with its portions made to overlap with each other, the elongate bodies 42 may be inclined relative to the outer surface of the balloon 30, under pressing forces. In this case, when the balloon 30 is inflated, the overlapping is released, and the pressing forces which would incline the elongate bodies 42 disappear. As a result, residual stress in the balloon deformed portions 36 and the base material deformed portions 46 is relieved, and the long axes of the elongate bodies 42 can approach perpendicularity to the outer surface of the balloon 30.

When the long axis of the elongate body 42 approaches perpendicularity to the outer surface of the balloon 30, the elongate body 42 becomes liable to pierce the living body tissue. As a result, releasing property of the drug from the outer surface of the balloon 30 and transferability of the drug to the living body tissue can be enhanced, and the drug can be delivered to the living body tissue more effectively.

The plurality of elongate bodies 42 may be disposed regularly on the outer surface of the balloon 30. Alternatively, the plurality of elongate bodies 42 may be disposed irregularly on the outer surface of the balloon 30. In addition, the elongate bodies 42 whose angles relative to the balloon 30 approaches perpendicularity when the balloon 30 is inflated may be provided throughout the coating layer 40, or may be provided only in part of the coating layer 40. All the elongate bodies 42 may not necessarily be in such a form that their angles relative to the balloon 30 approach perpendicularity when the balloon 30 is inflated, and the elongate bodies 42 in other forms may be simultaneously present.

The amount of the drug contained in the coating layer 40 is not particularly limited; the amount in density is 0.1 $\mu g/mm^2$ to 10 $\mu g/mm^2$, preferably 0.5 $\mu g/mm^2$ to 5 $\mu g/mm^2$, more preferably 0.5 $\mu g/mm^2$ to 3.5 $\mu g/mm^2$, and still more preferably 1.0 $\mu g/mm^2$ to 3 $\mu g/mm^2$. The amount of the crystals in the coating layer 40 is not particularly limited, and is 5 crystals/(10 $\mu m^2$) to 500,000 crystals/(10 $\mu m^2$) (the number of crystals per 10 $\mu m^2$), preferably 50 crystals/(10 $\mu m^2$) to 50,000 crystals/(10 $\mu m^2$), and more preferably 500 crystals/(10 $\mu m^2$) to 5,000 crystals/(10 $\mu m^2$).

The plurality of elongate bodies 42 in which crystals have mutually independent long axes may be present in their combined state (i.e., the plurality of elongate bodies 42 are in contact with one another). In addition, the plurality of adjacent elongate bodies 42 may be present in contact with one another while forming different angles. The plurality of elongate bodies 42 may be located on the balloon surface with a space (a space where the crystal is not contained) between the plurality of elongate bodies 42. Both the plurality of elongate bodies 42 in the combined state and the plurality of mutually spaced independent elongate bodies 42 may be present on the surface of the balloon 30. The plurality of elongate bodies 42 may be disposed circumferentially and in brush-shaped form while having different long axis directions. Each of the elongate bodies 42 exists independently, and has a certain length, and one end (base end) of the length portion is fixed to the base material 41 or the balloon 30. The elongate body 42 does not form a composite structure with, and is not joined to, adjacent elongate bodies 42. The long axes of the crystals are substantially rectilinear. The elongate body 42 forms a predetermined angle relative to the surface which its long axis intersects and with which its base portion 45 makes contact.

In accordance with an exemplary embodiment, it can be preferable that the elongate bodies 42 are standing independently, without making contact with one another. The base portions 45 of the elongate bodies 42 may be in contact with other base portions 45 on the substrate of the balloon 30. Alternatively, the base portions 45 of the elongate bodies 42 may be independent, without making contact with other base portions 45, on the substrate of the balloon 30.

The elongate bodies 42 may be hollow or may be solid. Both hollow elongate bodies 42 and solid elongate bodies 42 may exist on the surface of the balloon 30. Where the elongate body 42 is hollow, at least a portion of the elongate body 42 near a top end 44 of the elongate body 42 is preferably hollow. A section of the elongate body 42 in a plane perpendicular (orthogonal) to the long axis of the elongate body 42 has a void (hollow portion). In the elongate body 42 thus having a void, the section of the elongate body 42 in a plane perpendicular (orthogonal) to the long axis is polygonal in shape. The polygon here is, for example, a triangle, a tetragon, a pentagon, or a hexagon. Therefore, the elongate bodies 42 are each formed as an elongate polyhedron which has a distal end (or a distal surface) and a proximal end (or a proximal surface) and in which a side surface between the distal end (or the distal surface) and the proximal end (or the proximal surface) is composed of a plurality of substantially plain surfaces. In addition, the elongate bodies 42 may be needle-like in shape. This crystalline morphological form (hollow elongate body crystalline morphological form) constitutes the whole part or at least part of a plane, at the surface of the base material 41 or the balloon 30 in contact therewith.

The length in the long axis direction of the elongate bodies 42 having the long axes is, for example, preferably 5 µm to 20 µm, more preferably 9 µm to 11 µm, and still more preferably around 10 µm. Note that the length in the long axis direction of the elongate bodies 42 can be defined as the length before spreading of cracks. The diameter of the elongate bodies 42 having the long axes is, for example, preferably 0.01 µm to 5 µm, more preferably 0.05 µm to 4 µm, and still more preferably 0.1 µm to 3 µm. Examples of the combination of length in the long axis direction and diameter of the elongate bodies 42 having the long axes include a combination of a diameter of 0.01 µm to 5 µm when the length is 5 µm to 20 µm, a combination of a diameter of 0.05 µm to 4 µm when the length is 5 µm to 20 µm, and a combination of a diameter of 0.1 µm to 3 µm when the length is 5 µm to 20 µm. The elongate bodies 42 having the long axes are rectilinear in the long axis direction of the elongate bodies 42, and may also be curved in curved line forms. Both rectilinear elongate bodies 42 and curved elongate bodies 42 may exist on the surface of the balloon 30.

The crystalline morphological form having the crystals having long axes as aforementioned accounts for not less than 50% by volume, preferably not less than 70% by volume, based on the whole of the drug crystals on the outer surface of the balloon 30.

The crystal particles having the long axes after the coating of the coating layer 40 and before the folding of the balloon 30 are formed not to lie flat but to stand in relation to the outer surface of the balloon 30. The base material 41 may exist in a region where the elongate bodies 42 are present and may not exist in a region where the elongate bodies 42 are absent. In the crystal particles in this instance, the angle of the crystal particles is changed by the pleating (the step of forming the balloon 30 with the wing portions 32) or the folding (the step of folding the wing portions 32), whereby the angles of the long axes of the crystal particles relative to the outer surface of the balloon 30 can be changed. Therefore, while the crystals which are formed in the manner of lying flat on the outer surface of the balloon 30 from the beginning are firmly attached (fixed) to the outer surface of the balloon 30 and/or the adjacent crystal particles, the crystal particles which are standing are not formed in the state of being physically fixed to the outer surface of the balloon 30 or the adjacent crystal particles. For this reason, the standing crystal particles are only positioned (arranged) in such a manner as to make contact with, for example, the outer surface of the balloon 30 or the adjacent crystal particles, and their positions can be changed on a three-dimensional basis. Accordingly, the crystal particles after the coating are formed such that the angles and positions of the crystal particles can be changed through the pleating or folding of the balloon 30. Part of the crystal particles may be embedded in the surface of the balloon 30.

The base material 41 is present in the state of being distributed into spaces between the plurality of elongate bodies 42 standing together. In regard of the proportions of the materials constituting the coating layer 40, the crystals of the water-insoluble drug preferably occupy a larger volume than that occupied by the base material 41. The excipient constituting the base material 41 does not form a matrix. The matrix is a layer which is configured by continuation of a comparatively high-molecular material (polymer or the like), which forms a network-like three-dimensional structure, and in which minute spaces are present. Therefore, the water-insoluble drug constituting the crystals is not adhered to the inside of a matrix material. Moreover, the water-insoluble drug constituting the crystals is not embedded in the matrix material.

The base material 41 is formed as a dried layer, after being applied in an aqueous solution state to the outer surface of the balloon 30. The base material 41 is amorphous. The base material 41 may be crystal particles. The base material 41 may exist as a mixture of an amorphous state with crystal particles. The base material 41 in FIG. 4 is in a state including crystal particles and/or particulate amorphous portions. The base material 41 is formed as a layer including the water-insoluble drug. Alternatively, the base material 41 may be formed as an independent layer that does not include the water-insoluble drug. The thickness of the base material 41 is 0.1 µm to 5 µm, preferably 0.3 µm to 3 µm, and more preferably 0.5 µm to 2 µm.

The layer including the elongate body crystalline morphological form is low in toxicity and high in stenosis inhibitory effect at the time of delivery into a body. The water-insoluble drug including the hollow elongate body crystalline morphological form has good property of penetration into tissue because of a small crystal unit size upon transfer of the drug to the tissue, and, since it has good solubility, it acts effectively and can inhibit stenosis. In addition, it is considered that the drug is less liable to remain in the tissue as large lumps (i.e., in a relatively large lump form) and, therefore, exhibits low toxicity.

In addition, the layer including the elongate body crystalline morphological form has a plurality of substantially uniform elongate bodies 42 having the long axes, and the elongate bodies 42 are substantially uniformly standing together on the surface with which their base portions 45 make contact. Therefore, the size (the length in the long axis direction) of the crystals transferred to the tissue is as small as approximately 10 µm. For this reason, the drug uniformly acts on the lesion affected area, with an enhanced property for penetration into the tissue. Furthermore, since the size of the crystals transferred is small, there is no possibility that an excess amount of the drug might remain at the affected area for an excess of time; for this reason, it is considered, the drug can exhibit a high stenosis inhibitory effect, without exhibiting toxicity.

The drug in the coating on the outer surface of the balloon 30 may include an amorphous phase. The crystals and the amorphous phase may be disposed regularly in the coating layer 40. Alternatively, the crystals and the amorphous phase may be disposed irregularly.

The protective sheath 15 is a member for restraining the drug from falling off the balloon 30, and is removed before the balloon catheter 10 is put to use. The protective sheath 15 is formed from a flexible material. Examples of the material which can be used here include thermoplastic resins such as polyolefins (e.g., polyethylene, polypropylene, polybutene, ethylene-propylene copolymers, ethylene-vinyl acetate copolymers, ionomers, or mixtures of two or more of them), flexible polyvinyl chloride resin, polyamides, polyamide elastomers, polyesters, polyester elastomers, polyurethane, fluororesins, etc., silicone rubbers, and latex rubbers.

Now, a balloon coating system for forming the coating layer 40 on the aforementioned balloon 30 will be described below. The present system includes a balloon coating apparatus 50 (see FIG. 7) for forming the coating layer 40 on the balloon 30, and a balloon folding apparatus 100 (see FIG. 9) for folding the balloon 30 formed with the coating layer 40. By use of the balloon coating apparatus 50, crystals of a water-insoluble drug that extend while having independent long axes are formed on the outer surface of the balloon 30. Thereafter, the balloon 30 is folded by the balloon folding apparatus 100, whereby the long axes of the elongate bodies 42 are inclined such as to extend along the outer surface of the balloon 30.

Figure 7:
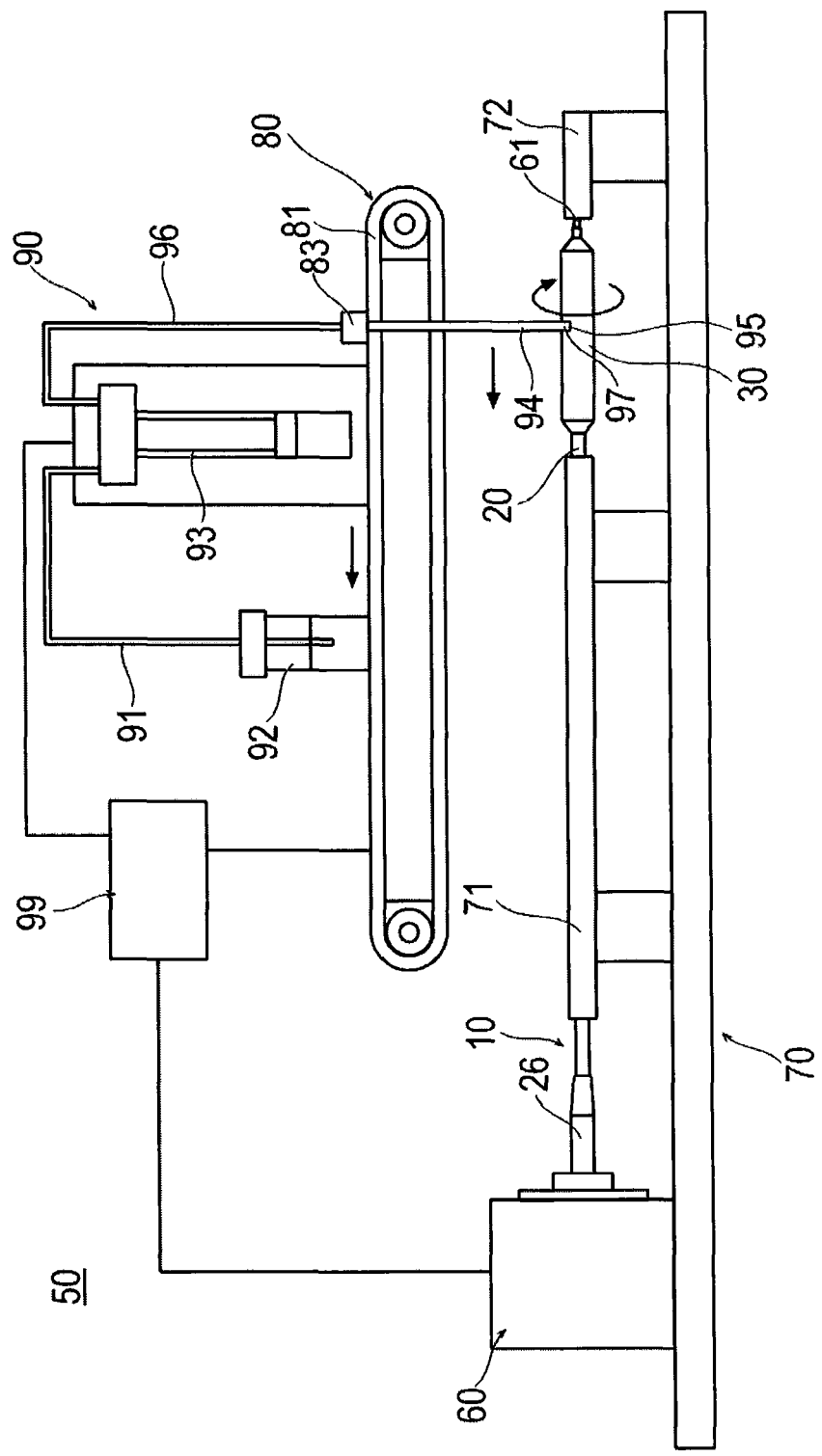
FIG. 7 is a front view of a balloon coating apparatus.
Figure 8:
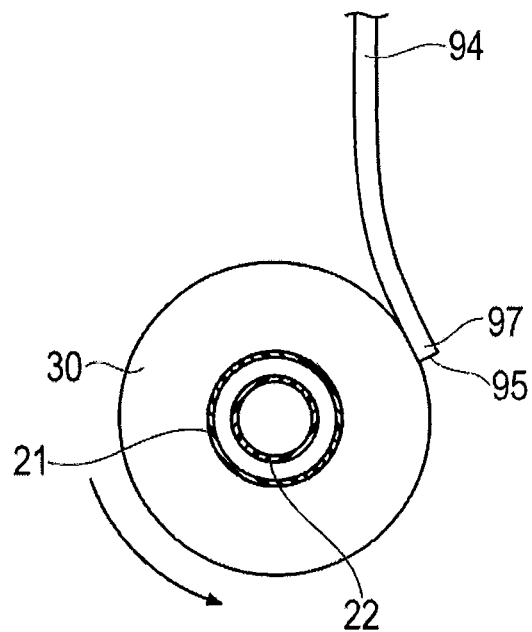
FIG. 8 is a sectional view of a dispensing tube in contact with the balloon.

In the first place, the balloon coating apparatus 50 will be described. As depicted in FIGS. 7 and 8, the balloon coating apparatus 50 includes a rotation mechanism section 60 for rotating the balloon catheter 10, and a support base 70 for supporting the balloon catheter 10. The balloon coating apparatus 50 further includes an application mechanism section 90 provided with a dispensing tube 94 for applying a coating solution to an outer surface of the balloon 30, a movement mechanism section 80 for moving the dispensing tube 94 relative to the balloon 30, and a control unit 99 for controlling the balloon coating apparatus 50.

The rotation mechanism section 60 holds the hub 26 of the balloon catheter 10, and rotates the balloon catheter 10 around an axis of the balloon 30 by a drive source, such as a motor, incorporated in the rotation mechanism 60. The balloon catheter 10 is held, with a core member 61 inserted in the guide wire lumen 24, and the core member 61 prevents the coating solution from flowing into the guide wire lumen 24. In addition, in the balloon catheter 10, for operating the flow of a fluid into the inflation lumen 23, a three-way cock capable of operating the opening/closing of a passage or passages is connected to a proximal opening portion 27 of the hub 26.

The support base 70 includes a pipe-shaped proximal-side support section 71 that accommodates the catheter main body 20 in the support base 70 and rotatably supports the catheter main body 20, and a distal-side support section 72 that rotatably supports the core member 61. Note that the distal-side support section 72 may, if possible, rotatably support a distal portion of the catheter main body 20, instead of the core member 61.

The movement mechanism section 80 includes a movable base 81 which can be moved rectilinearly in a direction parallel to the axis of the balloon 30, and a tube fixing section 83 to which the dispensing tube 94 is fixed. The movable base 81 can be moved rectilinearly by a drive source, such as a motor, incorporated in the movable base 81. The tube fixing section 83 fixes an upper end of the dispensing tube 94 relative to the movable base 81. With the movable base 81 moved, therefore, the dispensing tube 94 is moved rectilinearly in a direction parallel to the axis of the balloon 30. In addition, the application mechanism section 90 is mounted on the movable base 81, and the movable base 81 moves the application mechanism section 90 rectilinearly in both directions (both senses) along the axis.

The application mechanism section 90 is a section that applies the coating solution to the outer surface of the balloon 30. The application mechanism section 90 includes a container 92 containing the coating solution, a feed pump 93 that feeds the coating solution at an arbitrary feed rate, and the dispensing tube 94 that applies the coating solution to the balloon 30.

The feed pump 93 is, for example, a syringe pump. Controlled by the control unit 99, the feed pump 93 can draw the coating solution from the container 92 through a suction tube 91, and feed the coating solution into the dispensing tube 94 through a supply tube 96 at an arbitrary feed rate. The feed pump 93 is disposed on the movable base 81, and can be moved rectilinearly by the movement of the movable base 81. Note that the feed pump 93 is not limited to the syringe pump so long as it can feed the coating solution, and may be, for example, a tube pump.

The dispensing tube 94 is a member which communicates with the supply tube 96 and discharges to the outer surface of the balloon 30 the coating solution supplied from the feed pump 93 through the supply tube 96. The dispensing tube 94 is a flexible circular pipe-shaped member. The dispensing tube 94 has its upper end fixed to the tube fixing section 83, extends downward in the vertical direction from the tube fixing section 83, and is formed with an opening portion 95 at a discharge end 97 which is its lower end. With the movable base 81 moved, the dispensing tube 94 can be moved rectilinearly in both directions (both senses) along the axial direction of the balloon catheter 10, together with the feed pump 93 disposed on the movable base 81. The dispensing tube 94 can supply the coating solution to the outer surface of the balloon 30, in the state of being bent by being pressed against the balloon 30.

Note that the dispensing tube 94 may not necessarily be circular pipe-shaped so long as it can supply the coating solution. In addition, the dispensing tube 94 may not necessarily extend in the vertical direction so long as it can discharge the coating solution through the opening portion 95.

The dispensing tube 94 is preferably formed from a flexible material such that contact burden on the balloon 30 can be reduced and that variations in the contact position attendant on the rotation of the balloon 30 can be absorbed by flexure of the dispensing tube 94. Examples of the applicable material for the dispensing tube 94 include polyolefins such as polyethylene, polypropylene, etc., cyclic polyolefins, polyesters, polyamides, polyurethane, and fluororesins such as PTFE (polytetrafluoroethylene), ETFE (tetrafluoroethylene-ethylene copolymer), PFA (tetrafluoroethylene-perfluoroalkyl vinyl ether copolymer), FEP (tetrafluoroethylene-hexafluoropropylene copolymer), etc., but the material is not particularly limited so long as it is flexible and deformable.

The outside diameter of the dispensing tube 94 is not particularly limited, and is, for example, 0.1 mm to 5.0 mm, preferably 0.15 mm to 3.0 mm, and more preferably 0.3 mm to 2.5 mm. The inside diameter of the dispensing tube 94 is not particularly limited, and is, for example, 0.05 mm to 3.0 mm, preferably 0.1 mm to 2.0 mm, and more preferably 0.15 mm to 1.5 mm. The length of the dispensing tube 94 is not particularly limited, and is preferably a length of not more than five times the balloon diameter, for example, 1.0 mm to 50 mm, preferably 3 mm to 40 mm, and more preferably 5 mm to 35 mm.

The control unit 99 is composed, for example, of a computer, which controls the rotation mechanism section 60, the movement mechanism section 80, and the application mechanism section 90. Therefore, the control unit 99 can control the rotating speed of the balloon 30, the moving speed of the dispensing tube 94 in the axial direction of the balloon 30, the drug discharge rate from the dispensing tube 94, and so on.

The coating solution supplied from the dispensing tube 94 to the balloon 30 is a solution or dispersion containing the constituent materials of the coating layer 40, and contains a water-insoluble drug, an excipient, an organic solvent, and water. After the coating solution is supplied to the outer surface of the balloon 30, the organic solvent and water volatilize, whereby a coating layer 40 including a plurality of elongate bodies which are crystals of the water-insoluble drug that extend while having independent long axes is formed on the outer surface of the balloon 30.

The viscosity of the coating solution is 0.5 cP to 1,500 cP, preferably 1.0 cP to 500 cP, and more preferably 1.5 cP to 100 cP.

The water-insoluble drug means a drug which is insoluble or difficultly soluble in water; specifically, the water-insoluble drug is a drug of which the solubility in water is, for example, less than 5 mg/mL at pH 5 to 8. The solubility may be less than 1 mg/mL, or, further, may be less than 0.1 mg/mL. The water-insoluble drug includes fat-soluble drugs.

Some preferred examples of the water-insoluble drug include immunosuppressants, e.g., cyclosporines inclusive of cyclosporine, immunoadjuvants such as rapamycin, carcinostatics such as paclitaxel, antiviral or antibacterial agents, antineoplastic agents, analgesic and anti-inflammatory agents, antibiotics, antiepileptics, anxiolytic agents, antiparalytic agents, antagonists, neuron blocking agents, anticholinergic and cholinergic agents, muscarine antagonists and muscarine agents, antiadrenergic agents, antiarrhythmic agents, antihypertensive agents, hormone preparations, and nutritional supplements.

The water-insoluble drug is preferably at least one selected from a group composed of rapamycin, paclitaxel, docetaxel, and everolimus. The rapamycin, paclitaxel, docetaxel and everolimus herein include their analogs and/or derivatives so long as the analogs and/or derivatives have equivalent drug activity to the original. For example, paclitaxel and docetaxel are in an analog relation. Rapamycin and everolimus are in a derivative relation. Among these, more preferable is paclitaxel.

The excipient constitutes the base material 41 on the balloon 30. The excipient includes a water-soluble low-molecular compound. The molecular weight of the water-soluble low-molecular compound is 50 to 2,000, preferably 50 to 1,000, more preferably 50 to 500, and still more preferably 50 to 200. The amount of the water-soluble low-molecular compound is preferably 5 parts by mass to 10,000 parts by mass, more preferably 5 parts by mass to 200 parts by mass, and still more preferably 8 parts by mass to 150 parts by mass, per 100 parts by mass of the water-insoluble drug. Examples of the applicable constituent material of the water-soluble low-molecular compound include serine ethyl ester, citric acid esters, polysorbates, water-soluble polymers, sugars, contrast agents, amino acid esters, glycerol esters of short-chain monocarboxylic acids, pharmaceutically acceptable salts and surfactants, and mixtures of two or more of these. The water-soluble low-molecular compound is characterized in that it has a hydrophilic group and a hydrophobic group and is soluble in water. Preferably, the water-soluble low-molecular compound is non-swellable or difficultly swellable. The excipient is preferably amorphous on the balloon 30. The excipient including the water-soluble low-molecular compound has an effect of uniformly dispersing the water-insoluble drug on the outer surface of the balloon 30. The excipient constituting the base material 41 is preferably not a hydrogel. Being the low-molecular compound, the base material 41 is rapidly dissolved without being swelled upon contact with an aqueous solution. Further, since the base material 41 becomes easily soluble upon inflation of the balloon 30 in a blood vessel, the crystal particles of the water-insoluble drug on the outer surface of the balloon 30 become easily releasable; thus, the base material 41 has an effect of increasing the amount of the crystal particles of the drug adhered to the blood vessel. In the case where the base material 41 is a matrix composed of a contrast agent such as Ultravist®, the crystal particles are embedded in the matrix, and crystals are not produced to extend from the substrate of the balloon 30 toward the outside of the matrix. On the other hand, the elongate bodies 42 according to the present embodiment extend from the surface of the substrate of the balloon 30 to the outside of the base material 41. The length of that portion of the elongate body 42 which is located on the outside of the base material 41 is greater than the length of that portion of the elongate body 42 which is located inside the base material 41. The base material 41 is formed in such a manner as to support the base portions 45 of the elongate bodies 42 which are crystals.

The organic solvent is not particularly limited, and examples of the organic solvent include tetrahydrofuran, acetone, glycerin, ethanol, methanol, dichloromethane, hexane, and ethyl acetate. Among these, preferred are mixed solvents of some of tetrahydrofuran, ethanol, and acetone.

Examples of mixture of organic solvent with water include a mixture of tetrahydrofuran with water, a mixture of tetrahydrofuran and ethanol with water, a mixture of tetrahydrofuran and acetone with water, a mixture of acetone and ethanol with water, and a mixture of tetrahydrofuran and acetone and ethanol with water.

A method of forming crystals of the water-insoluble drug on the outer surface of the balloon 30 by use of the aforementioned balloon coating apparatus 50 will be described below.

First, the inflation fluid is supplied into the balloon 30 through the three-way cock connected to the proximal opening portion 27 of the balloon catheter 10. Next, in a state where the balloon 30 is inflated, the three-way cock is operated to seal up the inflation lumen 23, thereby maintaining the balloon 30 in the inflated state. The balloon 30 is inflated with a pressure (e.g., 4 atm) lower than a pressure (e.g., 8 atm) at the time of use in a blood vessel. Note that the coating layer 40 can also be formed on the outer surface of the balloon 30 without inflating the balloon 30, and, in that case, it is unnecessary to supply the inflation fluid into the balloon 30.

Subsequently, in a state in which the dispensing tube 94 does not make contact with the outer surface of the balloon 30, the balloon catheter 10 is rotatably disposed on the support base 70, and the hub 26 is interlocked with the rotation mechanism section 60.

Next, the position of the movable base 81 is adjusted to position the dispensing tube 94 in relation to the balloon 30. In this instance, the dispensing tube 94 is positioned to a position on the most distal side on the balloon 30 where to form the coating layer 40. As an example, the extending direction (discharge direction) of the dispensing tube 94 is opposite to the rotating direction of the balloon 30. Therefore, at the position where the dispensing tube 94 is put in contact with the balloon 30, the balloon 30 is rotated in the direction opposite to the discharge direction in which the coating solution is discharged from the dispensing tube 94.

By this, a physical stimulus can be given to the coating solution, whereby formation of crystal nuclei of the drug crystal can be promoted. Since the extending direction (discharge direction) of the dispensing tube 94 toward the opening portion 95 is opposite to the rotating direction of the balloon 30, the crystals of the water-insoluble drug formed on the outer surface of the balloon 30 are liable to be formed including a morphological form in which the crystals include a plurality of elongate bodies having mutually independent long axes. Note that the extending direction of the dispensing tube 94 may not necessarily be opposite to the rotating direction of the balloon 30, and, hence, may be the same as or perpendicular to the rotating direction.

Subsequently, the coating solution is supplied to the dispensing tube 94 while adjusting the feed rate by the feed pump 93, the balloon catheter 10 is rotated by the rotation mechanism section 60, and the movable base 81 is moved so that the dispensing tube 94 is gradually moved proximally along the axial direction of the balloon 30. The coating solution discharged from the opening portion 95 of the dispensing tube 94 is applied to the outer circumferential surface of the balloon 30 while drawing a spiral, since the dispensing tube 94 is moved relative to the balloon 30.

The moving speed of the dispensing tube 94 is not particularly limited, and is, for example, 0.01 mm/second to 2 mm/second, preferably 0.03 mm/second to 1.5 mm/second, and more preferably 0.05 mm/second to 1.0 mm/second. The discharge rate of the coating solution from the dispensing tube 94 is not particularly limited, and is, for example, 0.01 µL/second to 1.5 µL/second, preferably 0.01 µL/second to 1.0 µL/second, and more preferably 0.03 µL/second to 0.8 µL/second. The rotating speed of the balloon 30 is not particularly limited, and is, for example, 10 rpm to 300 rpm, preferably 30 rpm to 250 rpm, and more preferably 50 rpm to 200 rpm. The diameter of the balloon 30 when coated with the coating solution is not particularly limited, and is, for example, 1 mm to 10 mm, preferably 2 mm to 7 mm.

Thereafter, the organic solvent contained in the coating solution applied to the outer surface of the balloon 30 volatilizes earlier than water. Therefore, the organic solvent volatilizes in a condition where the water-insoluble drug, the water-soluble low-molecular compound and water are left on the outer surface of the balloon 30. When the organic solvent thus volatilizes with water left in the coating, the water-insoluble drug is precipitated inside the water-soluble low-molecular compound that contains water, and crystals gradually grow from crystal nuclei, so that drug crystals of a morphological form in which the crystals include a plurality of elongate bodies 42 having mutually independent long axes are formed on the outer surface of the balloon 30. The base portions 45 of the elongate bodies 42 may be located on the outer surface of the balloon 30, on the outer surface of the base material 41, or in the inside of the base material 41 (see FIG. 4). After the organic solvent has volatilized and the drug crystals are precipitated as the plurality of elongate bodies 42, water evaporates more slowly than the organic solvent, and the base material 41 including the water-soluble low-molecular compound is formed. The time taken for evaporation of water is appropriately set in accordance with the kind of the drug, the kind of the water-soluble low-molecular compound, the kind of the organic solvent, the ratios of the amounts of the materials, the coating amount of the coating solution, and the like, and is, for example, approximately 1 seconds to 600 seconds.

Then, while rotating the balloon 30, the dispensing tube 94 is gradually moved in the axial direction of the balloon 30, whereby the coating layer 40 is gradually formed on the outer surface of the balloon 30 along the axial direction of the balloon 30. After the coating layer 40 is formed over the whole range of coating for the balloon 30, operations of the rotation mechanism section 60, the movement mechanism section 80 and the application mechanism section 90 are stopped.

Thereafter, the balloon catheter 10 is removed from the balloon coating apparatus 50, to complete the coating of the balloon 30.

Now, the balloon folding apparatus 100 will be described below. The balloon folding apparatus 100 is an apparatus capable of folding the balloon 30 in the manner of winding around the inner tube 22.

Figure 9:
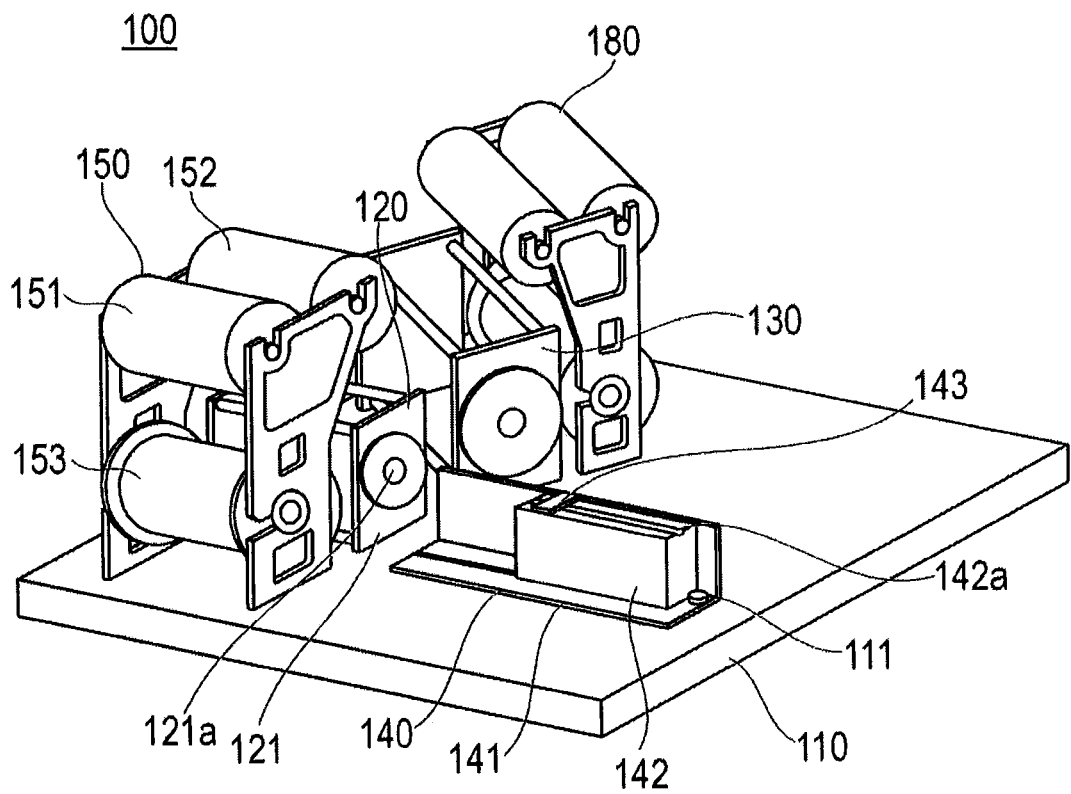
FIG. 9 is a perspective view of a balloon folding apparatus.

As depicted in FIG. 9, the balloon folding apparatus 100 has a pleating section 120, a folding section 130 and a support base 140 which are disposed on a base 110 formed in a base shape. The pleating section 120 is capable of forming the balloon 30 with wing portions 32 projecting in radial directions. The folding section 130 is capable of folding the wing portions 32 formed in the balloon 30, in the manner of lying flat in the circumferential direction. The support base 140 is capable of mounting and holding the balloon catheter 10 thereon. The wing portions 32 formed in the balloon 30 are formed by pleats extending substantially in an axial direction of the balloon 30, such that the pleats project in the circumferential direction from a long axis of the balloon 30 when viewed in a section perpendicular to the axis of the balloon 30. The length in the long axis direction of the wing portions 32 does not exceed the length of the balloon 30. The length of the wing portions 32 in the direction of projecting in the circumferential direction of the catheter main body 20 is 1 to 8 mm. The number of the wing portions 32 is not particularly limited, it can be selected from among the numbers of two to seven, and it is three in the present embodiment.

On the base 110, a film supply section 150 that supplies a first film 155 and a second film 156 to the pleating section 120 is disposed adjacently to the pleating section 120. In addition, on the base 110, a film supply section 180 that supplies a first film 181 and a second film 182 to the folding section 130 is disposed adjacently to the folding section 130.

The pleating section 120 has a front surface plate 121 perpendicular to the base 110, and the front surface plate 121 has an insertion hole 121a into which a distal portion of the balloon catheter 10 can be inserted. In addition, the folding section 130 has a front surface plate 131 perpendicular to the base 110, and the front surface plate 131 has an insertion hole 131a into which the distal portion of the balloon catheter 10 can be inserted. The front surface plate 131 of the folding section 130 faces in a direction different by a predetermined angle from the direction in which the front surface plate 121 of the pleating section 120 faces.

On that side of the support base 140 which is remote from the pleating section 120 and the folding section 130, a support shaft 111 projecting upward from the base 110 is pivotally mounted. The support base 140, by sliding movement on an upper surface of the base 110 with the support shaft 111 as a center, can be positioned in a position for facing the front surface plate 121 of the pleating section 120 and a position for facing the front surface plate 131 of the folding section 130.

The support base 140 has a base section 141 mounted on the base 110, and a holding base section 142 horizontally movable on the base section 141. The base section 141 is slidable on the upper surface of the base 110. The holding base section 142 can be advanced or retracted in relation to (in regard of a direction toward) the pleating section 120 or the folding section 130, by sliding movement on the upper surface of the base section 141.

An upper surface of the holding base section 142 is formed with a groove-shaped mounting section 142a on which the catheter main body 20 of the balloon catheter 10 can be mounted. In addition, the holding base section 142 is provided with a holding section 143 in such a manner as to cover a part of the mounting section 142a from above. The holding section 143 is capable of fixing by holding the catheter main body 20 of the balloon catheter 10 mounted on the mounting section 142a. Note that the balloon catheter 10 may be fixed by other method so long as the balloon catheter 10 can be fixed.

In a state in which the support base 140 faces the front surface plate 121 of the pleating section 120, the center of the insertion hole 121a formed in the front surface plate 121 is located on an extension line of the mounting section 142a of the holding base section 142. Therefore, the balloon catheter 10 with the catheter main body 20 mounted on the mounting section 142a is inserted into the inside of the pleating section 120 through the center position of the insertion hole 121a. In a state in which the support base 140 faces the front surface plate 131 of the folding section 130, the center of the insertion hole 131a formed in the front surface plate 131 is located on an extension line of the mounting section 142a of the holding base section 142. Therefore, the balloon catheter 10 with the catheter main body 20 mounted on the mounting section 142a is inserted into the inside of the folding section 130 through the center position of the insertion hole 131a, by sliding movement of the holding base section 142 on the base section 141.

Figure 10:
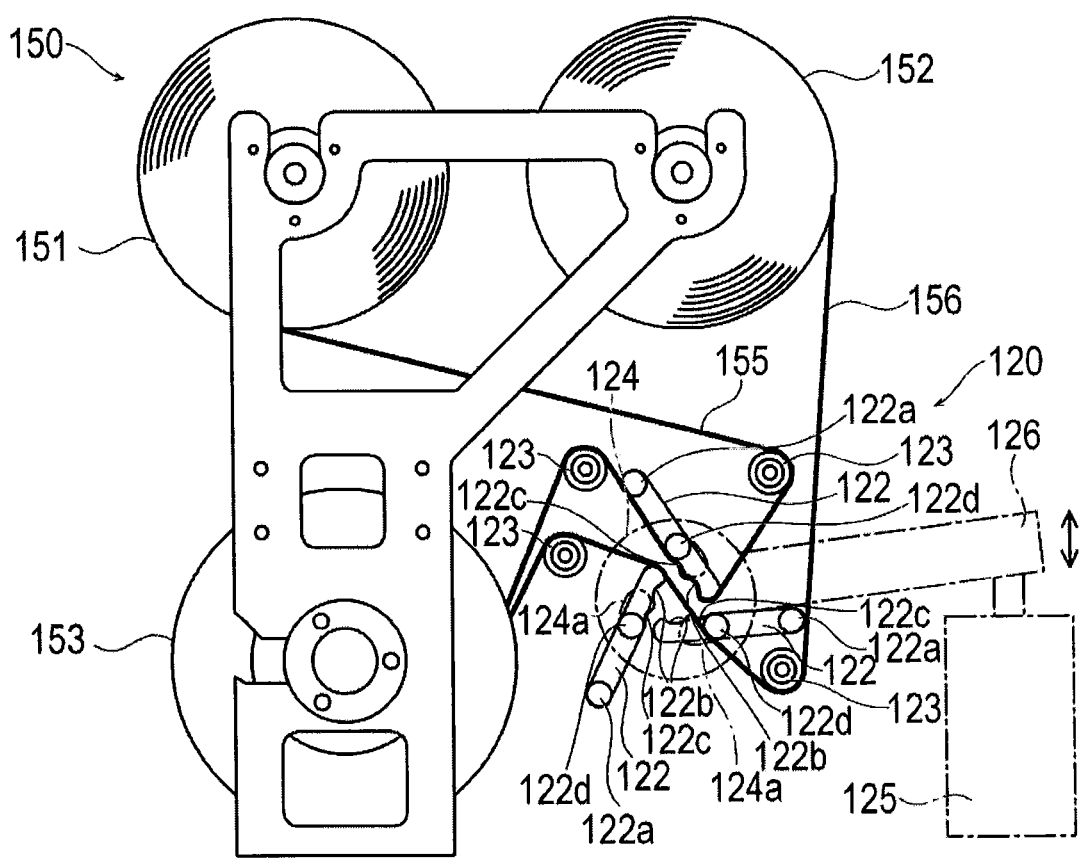
FIG. 10 is a front view depicting the layout of blades and a film supply section of a pleating section.

Now, the structure of the pleating section 120 will be described below. As depicted in FIG. 10, the pleating section 120 has three blades 122 (wing-forming members) in the inside of the pleating section 120. Each of the blades 122 is a plate-shaped member formed to have an equal sectional shape at positions along the axial direction of the balloon catheter 10 inserted. The blades 122 are disposed at mutual angles of 120 degrees, with the center position of insertion of the balloon 30 as a reference. In other words, the blades 122 are disposed at regular angular intervals along the circumferential direction. The blade 122 has a rotary movement center portion 122a near its outer circumferential end, and can be moved rotationally around the rotary movement center portion 122a. In addition, the blade 122 has a moving pin 122d extending in the axial direction, on the inner circumference side relative to the rotary movement center portion 122a. The moving pin 122d is fitted in a fitting groove 124a formed in a rotary member 124 which is rotatable inside the pleating section 120. The rotary member 124 is interlocked with a beam section 126 extending substantially horizontally. The rotary member 124 can be moved rotationally by receiving a rotating force from the beam section 126 which is inclined by receiving a force from a drive source 125 such as a hydraulic cylinder or a motor. When the rotary member 124 is rotated, the moving pins 122d fitted in the fitting grooves 124a are moved in the circumferential direction, whereby each of the blades 122 is moved rotationally around the rotary movement center portion 122a of the rotary member 124. With the three blades 122 moved rotationally, a space region in a central area surrounded by the blades 122 can be narrowed. Note that the number of the blades 122 is not particularly limited so long as it is not less than two.

The blade 122 has a first shape forming portion 122b and a second shape forming portion 122c, which are substantially arcuate in shape, at its inner circumferential end portions on the side opposite to the rotary movement center portion 122a. As the blade 122 is moved rotationally, the first shape forming portion 122b comes into contact with a surface of the balloon 30 inserted in the pleating section 120, whereby the balloon 30 can be formed with the wing portion 32 projecting in a radial direction. As the blade 122 is rotated, the second shape forming portion 122c comes into contact with the wing portion formed in the balloon 30, whereby the wing portion 32 can be curved in a predetermined direction. In addition, the pleating section 120 has a heater (not depicted) for heating the blades 122. The length of the blade 122 along the axial direction of the balloon catheter 10 is greater than the length of the balloon 30. In addition, the lengths of the first shape forming portion 122b and the second shape forming portion 122c of the blade 122 may range or may not range over the whole length of the blade 122.

The blades 122 are supplied from the film supply section 150 with the first film 155 and the second film 156 which are made of resin. For guiding each of the films, a plurality of rotary shaft portions 123 are provided in the pleating section 120. The first film 155 is passed from a first film holding section 151 and through the rotary shaft section 123, to be engaged on a surface of the blade 122 disposed at an upper portion. In addition, the first film 155 is passed from the blade 122 and through the rotary shaft section 123, to reach a film take-up section 153 which is rotationally driven by a drive source such as a motor not depicted. The second film 156 is passed from a second film holding section 152 and through the rotary shaft section 123, to be engaged on the two blades 122 disposed at lower portions. In addition, the second film 156 is passed through the rotary shaft section 123, to reach the film take-up section 153. By these, a state is established in which the center position of the pleating section 120 in which the balloon 30 is inserted and passed is surrounded by the first film 155 and the second film 156.

The first film 155 and the second film 156 have a function of protecting the balloon 30 by preventing the balloon 30 from making direct contact with the surfaces of the blades 122 when the balloon 30 is inserted into the pleating section 120 and the blades 122 are moved rotationally to form the balloon 30 with the wing portions 32. After the wing portions 32 of the balloon 30 are formed, the first film 155 and the second film 156 are taken up onto the film take-up section 153 by a predetermined length. In other words, those portions of the first film 155 and the second film 156 which have once made contact with the balloon 30 do not make contact with the balloon 30 again, and, each time the balloon 30 is inserted, new portions of the films are supplied to the center position of the pleating section 120.

Figure 11:
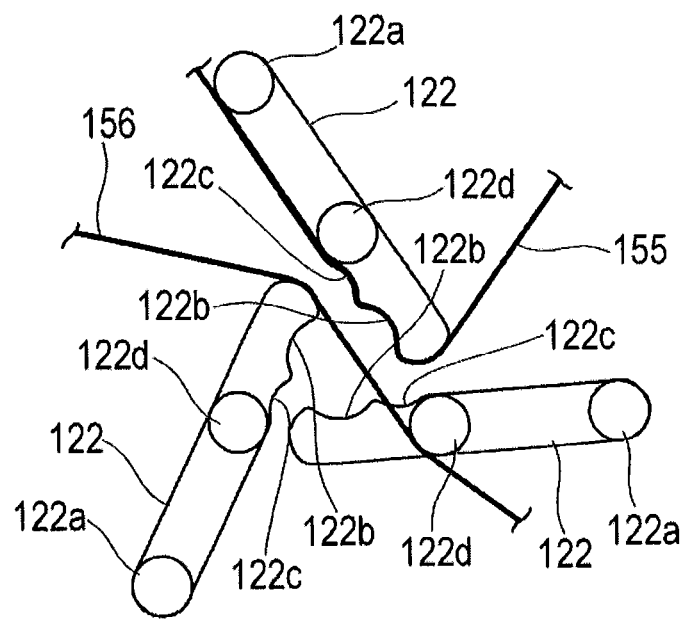
FIG. 11 is a front view of the blades in the pleating section.

As depicted in FIG. 11, in a state before the insertion of the balloon 30, the first shape forming portions 122b and the second shape forming portions 122c of the three blades 122 are spaced from one another. A central region among the blades 122 is surrounded by the first shape forming portions 122b which are substantially arcuate in shape, and the balloon 30 before folded can be inserted in a central region among the blades 122.

Figure 12:
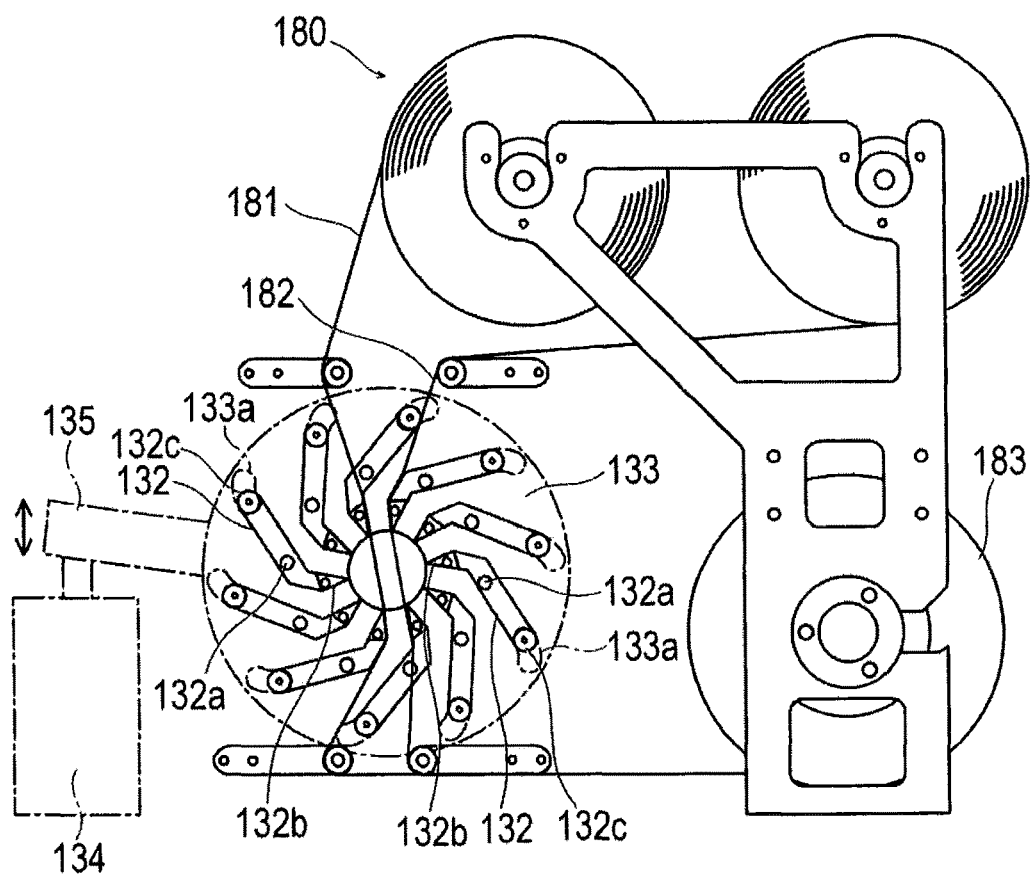
FIG. 12 is a front view depicting the layout of blades and a film supply section of a folding section.

Now, the structure of the folding section 130 will be described below. As depicted in FIG. 12, the folding section 130 has ten blades 132 (wing-folding members) in the inside of the folding section 130. Each of the blades 132 is a plate-shaped member formed to have an equal sectional shape at positions along the axial direction of the balloon catheter 10 inserted. The blades 132 are disposed at mutual angles of 36 degrees, with the center position of insertion of the balloon 30 as a reference. In other words, the blades 132 are disposed at regular angular intervals along the circumferential direction. The blade 132 has a rotary movement center portion 132a near its center, and can be moved rotationally around the rotary movement center portion 132a. In addition, each blade 132 has a moving pin 132c extending in the axial direction, near its outer circumferential end. The moving pin 132c is fitted in a fitting groove 133a formed in a rotary member 133 which is rotatable inside the folding section 130. The rotary member 133 is interlocked with a beam 135 extending substantially horizontally. The rotary member 133 can be moved rotationally by receiving a rotating force from the beam 135 which is inclined by receiving a force from a drive source 134 such as a hydraulic cylinder or a motor. When the rotary member 133 is rotated, the moving pins 132c fitted in the fitting grooves 133a are moved in the circumferential direction, whereby each of the blades 132 is moved rotationally around the rotary movement center portion 132a of the rotary member 133. With the ten blades 132 moved rotationally, a space region in a central area surrounded by the blades 132 can be narrowed. Note that the number of the blades 132 is not limited to ten.

The blade 132 is bent on a tip side, and its tip portion 132b is sharp in shape. As the blades 132 are moved rotationally, the tip portions 132b come into contact with the surface of the balloon 30 inserted into the folding section 130, whereby the wing portions 32 formed in the balloon 30 can be folded in the manner of lying flat in the circumferential direction. In addition, the folding section 130 has a heater (not depicted) for heating the blades 132.

The blades 132 are supplied from the film supply section 180 with the first film 181 and the second film 182 which are made of resin. A supplying structure for each film is the same as that in the case of the pleating section 120. The first film 181 and the second film 182 are disposed to face each other such that a central space region surrounded by the blades 132 is interposed between the first film 181 and the second film 182. By the first film 181 and the second film 182, the balloon 30 inserted in the folding section 130 can be prevented from making direct contact with the surfaces of the blades 132. The first film 181 and the second film 182 are passed through the blades 132, to reach a film take-up section 183 which is rotationally driven by a drive source such as a motor not depicted.

Figure 13:
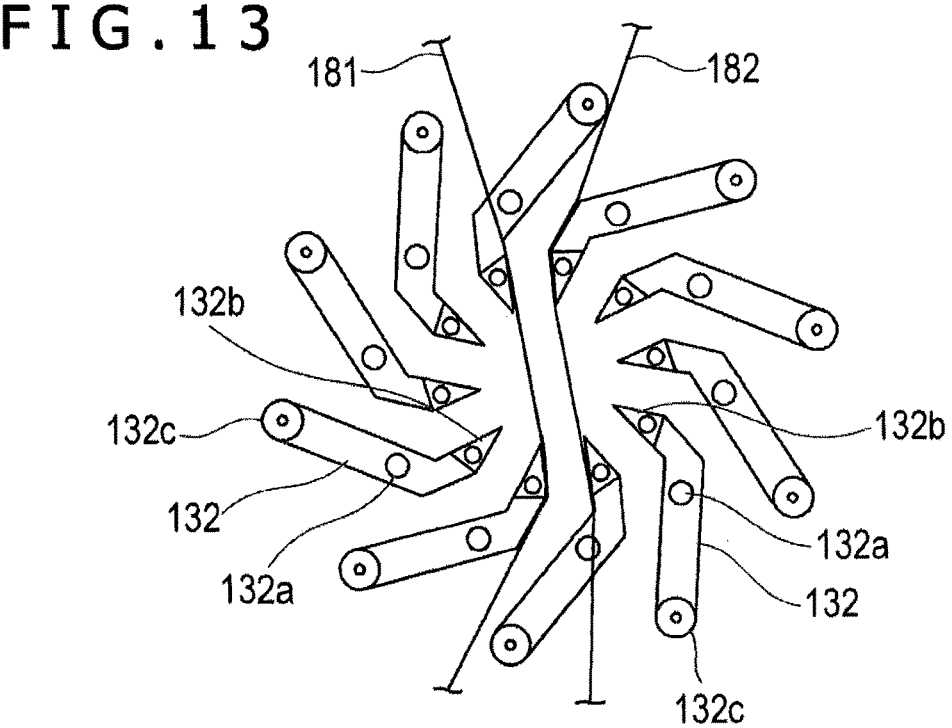
FIG. 13 is a front view of the blades in the folding section.

As depicted in FIG. 13, in a state before insertion of the balloon 30, the tip portions 132b of the blades 132 are in the state of being spaced from one another in the circumferential direction. In a central region which is surrounded by the blades 132 and is located between the first film 181 and the second film 182, the balloon 30 formed with the wing portions 32 can be inserted.

Now, a method of folding the balloon 30 formed on its outer surface with crystals of a drug by the balloon coating apparatus 50, by use of the balloon folding apparatus 100, will be described below.

First, for forming the balloon 30 with the wing portions 32, the catheter main body 20 is mounted on the mounting section 142a of the support base 140 and is held by the holding section 143. An inflation fluid is injected into the balloon 30 through the three-way cock (i.e., three-way value) attached to the hub 26, the hub 26 and the inner tube 22, whereby the balloon 30 is put into a state of being inflated to a certain extent. In addition, the blades 122 in the pleating section 120 are heated. The core member 61 is inserted in the guide wire lumen 24. By the core member 61, the catheter main body 20 is restrained from flexure due to the weight of the catheter main body 20.

Figure 14:
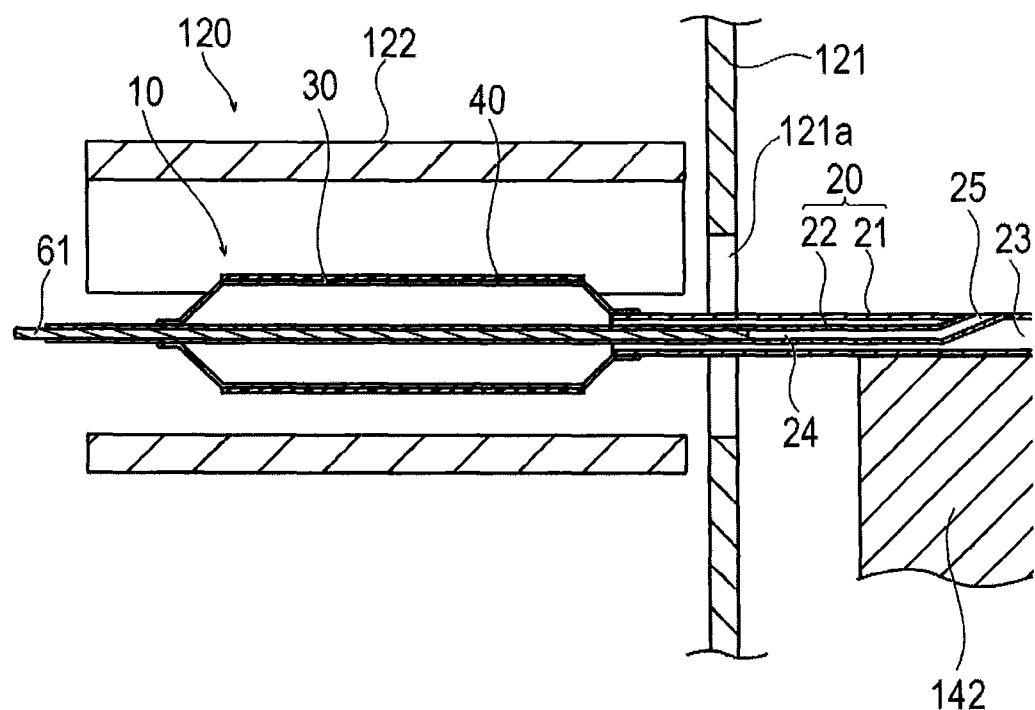
FIG. 14 is a sectional view of a balloon catheter disposed in the pleating section.

Next, as depicted in FIG. 14, the holding base section 142 is moved sliding on the base section 141, to insert the balloon catheter 10 into the pleating section 120 through the insertion hole 121a.

Figure 15:
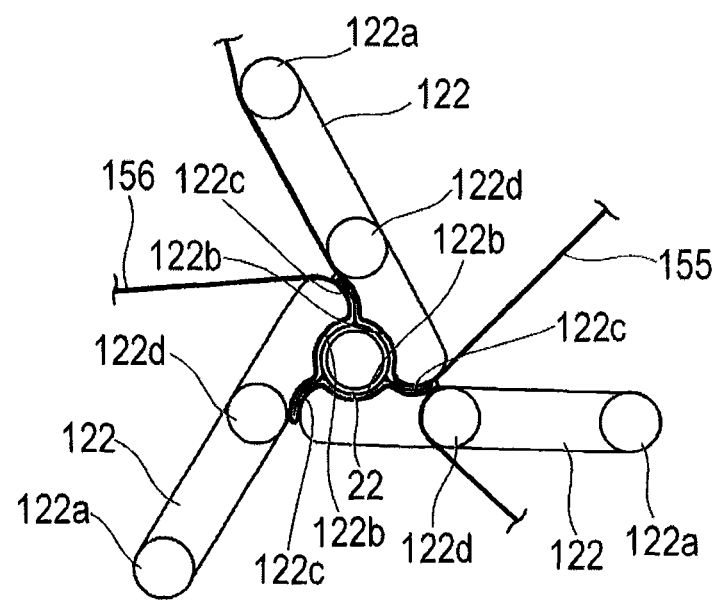
FIG. 15 is a front view depicting the blades in the pleating section in a state in which the balloon is formed with wing portions by rotationally moving the blades.

Subsequently, the drive source 125 is operated to rotate the rotary member 124 (see FIG. 12), whereon as depicted in FIG. 15, the blades 122 are moved rotationally, and the first shape forming portions 122b of the blades 122 approach one another, so that the central region among the blades 122 is narrowed. Attendant on this, the balloon 30 inserted in the central region among the blades 122 is pressed against the inner tube 22 by the first shape forming portions 122b. That portion of the balloon 30 which is not pressed by the first shape forming portion 122b is pushed out into a gap between a tip portion of one blade 122 and the second shape forming portion 122c of the blade 122 adjacent to the one blade 122, whereby the wing portion 32 curved to one side is formed. Since the balloon 30 is heated to approximately 50 degrees to 60 degrees by the blades 122, the wing portions 32 thus formed can maintain their shapes. In this way, the balloon 30 is formed with three wing portions 32 along the circumferential direction.

In this instance, those surfaces of each blade 122 which make contact with the balloon 30 are covered by the first film 155 and the second film 156, so that the balloon 30 does not make direct contact with the surfaces of the blades 122. After the balloon 30 is formed with the wing portions 32, the blades 122 are moved rotationally in the manner of returning into their original positions, and the balloon 30 is withdrawn out of the pleating section 120. Note that since the internal volume of the balloon 30 is reduced in the process of pleating, it is preferable to regulate the three-way cock according to the volume reduction, to discharge the inflation fluid to the outside, thereby deflating the balloon 30. By this, an excessive force can be restrained (or prevented) from acting on the balloon 30.

Figure 18A:
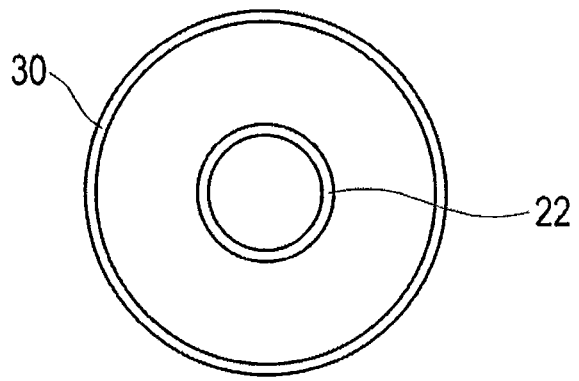
Figure 18B:
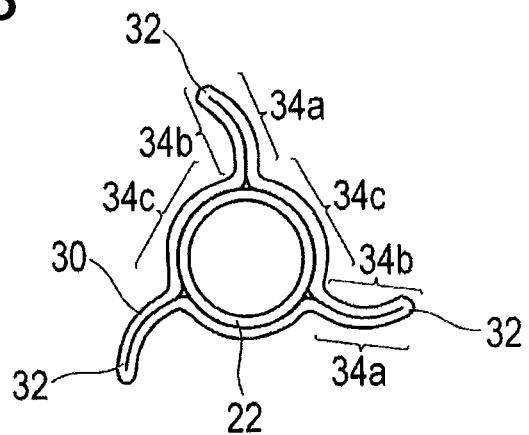

As depicted in FIG. 18A, the balloon 30 has a substantially circular sectional shape in a state in which the inflation fluid has been injected into the balloon 30. By being formed with the projecting wing portions 32, starting from this state, the balloon 30 is formed with: wing outer portions 34a that have been pressed by the second shape forming portions 122c and constitute outside surfaces of the wing portions 32; wing inner portions 34b that are pressed by tip portions of the blades 122 and constitute inside surfaces of the wing portions 32; and intermediate portions 34c that have been pressed by the first shape forming portions 122b and are located between the coating layer wing outer portions 34a and the wing inner portions 34b, as depicted in FIGS. 15 and 18B. Note that in the process of pleating, the balloon 30 is pressed by the blades 122 while deflating the balloon 30 for forming the wing portions 32, and, therefore, there is no need for strong pressing forces by the blades 122. Accordingly, even when the balloon 30 is pressed by the blades 122, the structure of the crystals formed on the surface of the balloon 30 is changed relatively little.

Figure 16:
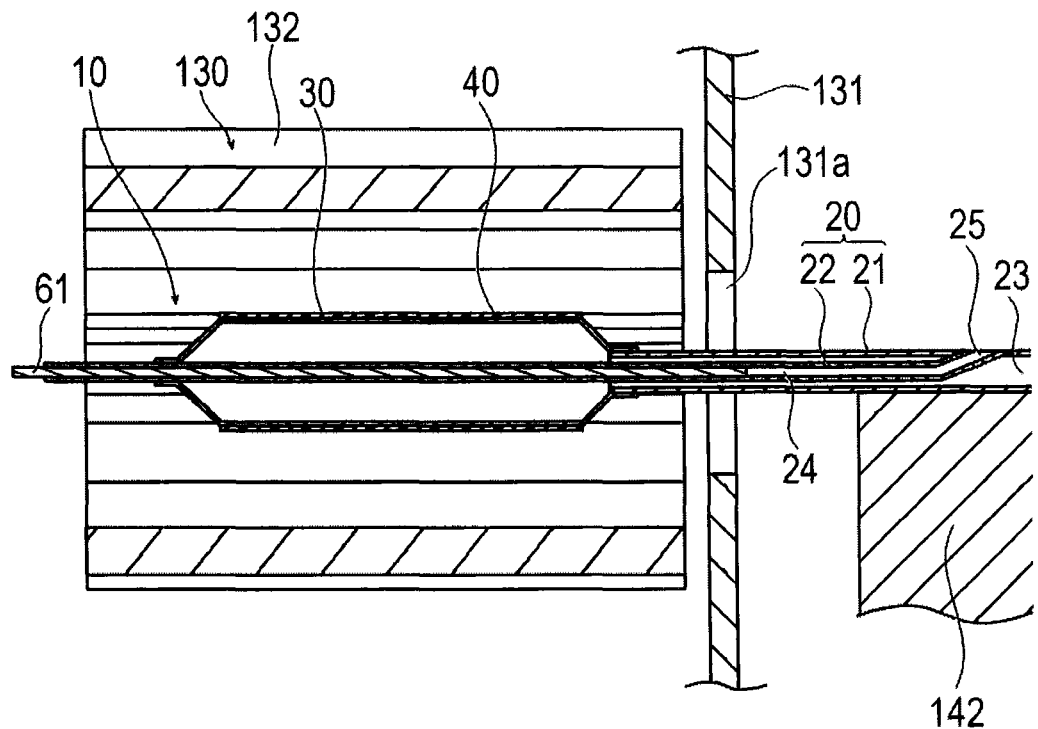
FIG. 16 is a sectional view of the balloon catheter disposed in the folding section.

Next, the holding base section 142 is moved on the upper surface of the base section 141 to be spaced from the pleating section 120, and the balloon catheter 10 is withdrawn out of the pleating section 120. Subsequently, the support base 140 is moved sliding on the upper surface of the base 110, whereby the support base 140 is positioned at a position for facing the front surface plate 131 of the folding section 130. Thereafter, the holding base section 142 is moved on the upper surface of the base section 141, whereby the balloon catheter 10 is inserted into the folding section 130 through the insertion hole 131a, as depicted in FIG. 16. The blades 132 in the folding section 130 have already been heated to approximately 50 to 60 degrees.

Figure 17:
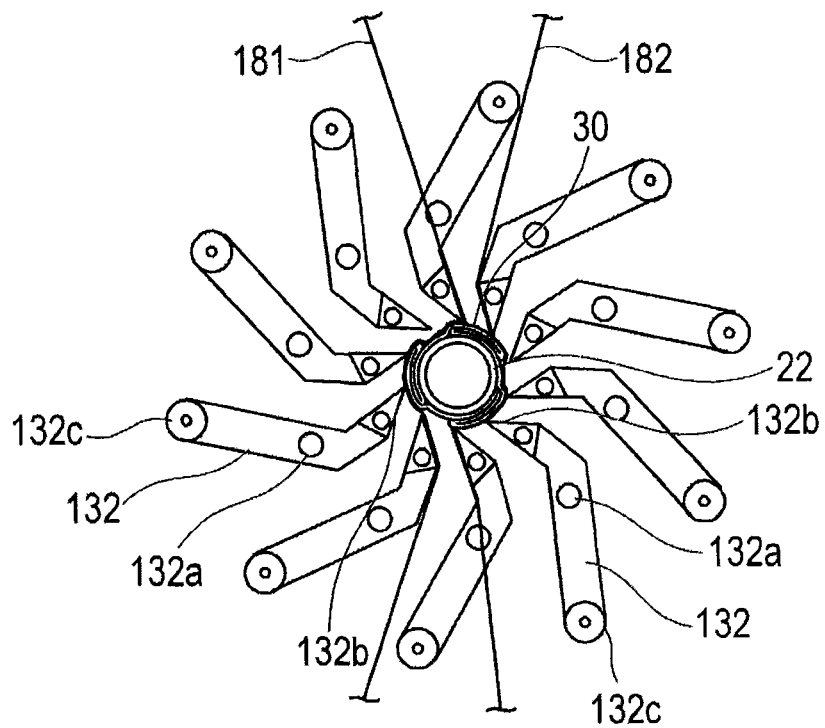
FIG. 17 is a front view depicting the blades in the folding section in a state in which the wing portions of the balloon are folded by rotationally moving the blades.

After the balloon 30 formed with the wing portions 32 is inserted into the folding section 130, the drive source 134 is operated to rotate the rotary member 133, as depicted in FIG. 17, whereon the blades 132 are moved rotationally, and the tip portions 132b of the blades 132 approach one another, so that a central region among the blades 132 is narrowed. Attendant on this, the balloon 30 inserted in the central region among the blades 132 is put into a state in which the wing portions 32 are laid flat in the circumferential direction by the tip portions 132b of the blades 132. Since the blades 132 have been preliminarily heated before insertion of the balloon 30 and the balloon 30 is heated by the blades 132, the wing portions 32 laid flat in the circumferential direction by the blades 132 can maintain their shapes. In this instance, those surfaces of each blade 132 which make contact with the balloon 30 are covered by the first film 181 and the second film 182, so that the balloon 30 does not make direct contact with the surfaces of the blades 132.

Figure 18C:
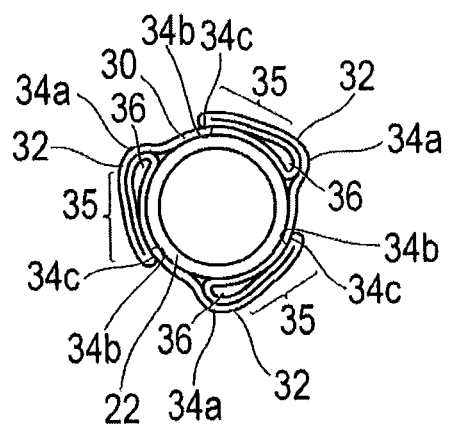

When the wing portions 32 of the balloon 30 are folded, the wing inner portions 34b and the intermediate portions 34c are laid on each other and make contact with each other, to form overlapping portions 35 in which portions of the outer surface of the balloon 30 face each other and overlap with each other, as depicted in FIGS. 17 and 18C. In addition, part of the intermediate portion 34c and the wing outer portion 34a are not covered by the wing inner portion 34b, but are exposed to the outside. In addition, in the state in which the balloon 30 is folded, a root-side space portion 36 is formed between a root portion of the wing portion 32 and the intermediate portion 34c. In the region of the root-side space portion 36, a minute gap is formed between the wing portion 32 and the intermediate portion 34c. On the other hand, that region of the wing portion 32 which is located on the tip side relative to the root-side space portion 36 is in the state of being in close contact with the intermediate portion 34c. The proportion of the circumferential length of the root-side space portion 36 to the circumferential length of the wing portion 32 is in the range from 1% to 95%. The wing outer portions 34a of the balloon 30 receive pressing forces in the manner of rubbing in the circumferential direction from the first film 181 and the second film 182 both pressed by the blades 132, thereby being heated further. As a result of this, the elongate bodies 42 provided on the wing outer portions 34a have their long axes inclined relative to the outer surface of the balloon 30. Consequently, the base material 41 is formed with the base material deformed portions 46, and the balloon 30 is formed with the balloon deformed portions 36 (see FIGS. 3 to 5). Part of the elongate bodies 42 may be broken and thereby separated.

In addition, since the portions of the outer surface of the balloon 30 that overlap with each other at the overlapping portions 35 are not exposed to the outside, the pressing forces from the blades 132 act on the portions of the outer surface of the balloon 30 that overlap with each other at the overlapping portions 35 indirectly. Therefore, the forces acting on the elongate bodies 42 provided on the portions of the outer surface of the balloon 30 that overlap with each other at the overlapping portions 35 can be easily controlled such as not to become excessively strong. Accordingly, desirable forces for inclining the elongate bodies 42 relative to the outer surface of the balloon 30 can be made to act on the elongate bodies 42 provided on the portions of the outer surface of the balloon 30 that overlap with each other at the overlapping portions 35. For this reason, the portions of the outer surface of the balloon 30 that overlap with each other at the overlapping portions 35 can be formed with desirable base material deformed portions 46 and desirable balloon deformed portions 36, in such a manner that the angles of the long axes of the elongate bodies 42 relative to the balloon 30 approach perpendicularity when the balloon 30 is inflated. There is the possibility that the base material deformed portions 46 and the balloon deformed portions 36 may have residual stress left in the inside of the base material deformed portions 46 and the balloon deformed portions 36. In addition, in those regions of the wing inner portions 34b and the intermediate portions 34c facing each other which face the root-side space portion 36, namely, in the regions where the wing inner portion 34b and the intermediate portion 34c are not in close contact with each other, the elongate bodies 42 hardly receive pressing forces. In the regions where the wing inner portion 34b and the intermediate portion 34c are not in close contact with each other, therefore, the elongate bodies 42 are hardly inclined, and desirable base material deformed portions 46 and desirable balloon deformed portions 36 are hardly formed. In addition, in those regions of the wing inner portions 34b and the intermediate portions 34c facing each other which do not face the root-side space portion 36, namely, in the regions where the wing inner portion 34b and the intermediate portion 34c are in close contact with each other, the elongate bodies 42 are liable to receive pressing forces. In the regions where the wing inner portion 34b and the intermediate portion 34c are in close contact with each other, therefore, the elongate bodies 42 are liable to be inclined, and desirable base material deformed portions 46 and desirable balloon deformed portions 36 are liable to be formed. Note that part of the elongate bodies 42 may be broken, and thereby separated, at the overlapping portions 35. The elongate bodies 42 in a state of having their long axes along the outer surface of the balloon 30 are sandwiched between portions of the outer surface of the balloon 30 at the overlapping portions 35, and, therefore, this state is maintained favorably.

After the wing portions 32 of the balloon 30 are folded, the blades 132 are moved rotationally in the manner of returning into their original positions. Next, the balloon 30 is withdrawn out of the folding section 130. Subsequently, the holding of the catheter main body 20 by the holding section 143 is released, the balloon 30 is covered by the tubular protective sheath 15 (see FIG. 1), and the folding of the balloon 30 of the balloon catheter 10 is completed. The protective sheath 15 is a member for restraining the drug from falling off the balloon 30, and it is removed before the balloon catheter 10 is put to use.

A method of using the balloon catheter 10 according to the present embodiment will be described below, taking as an example a case of treating a stenosed part in a blood vessel.

First, by a known method such as a Seldinger method, the operator percutaneously punctures a blood vessel and places an introducer (not depicted) indwelling. Next, the protective sheath 15 of the balloon catheter 10 is removed, priming is performed, and thereafter a guide wire 200 (see FIG. 19) is inserted into the guide wire lumen 24. In this state, the guide wire 200 and the balloon catheter 10 are inserted into the blood vessel through the inside of the introducer. Subsequently, the balloon catheter 10 is moved forward, with the guide wire 200 preceding, and the balloon 30 is delivered to a stenosed part. Note that a guiding catheter may be used for delivering the balloon catheter 10 to the stenosed part 300.

When the balloon 30 is moved within a blood vessel, the overlapping portions 35 where portions of the outer surface of the balloon 30 overlap with each other are not liable (i.e., not likely) to make contact with the blood. Further, the elongate bodies 42 having their long axes inclined relative to the outer surface of the balloon 30 are not liable (i.e., not likely) to flow even when exposed to the blood, as compared to the case where their long axes are perpendicular to the outer surface. For this reason, the elongate bodies 42 which are drug crystals located at the overlapping portions 35 are not exposed to the blood, or are restrained from flowing out into the blood even if exposed to the blood, so that they are effectively delivered to the target position.

Figure 19:
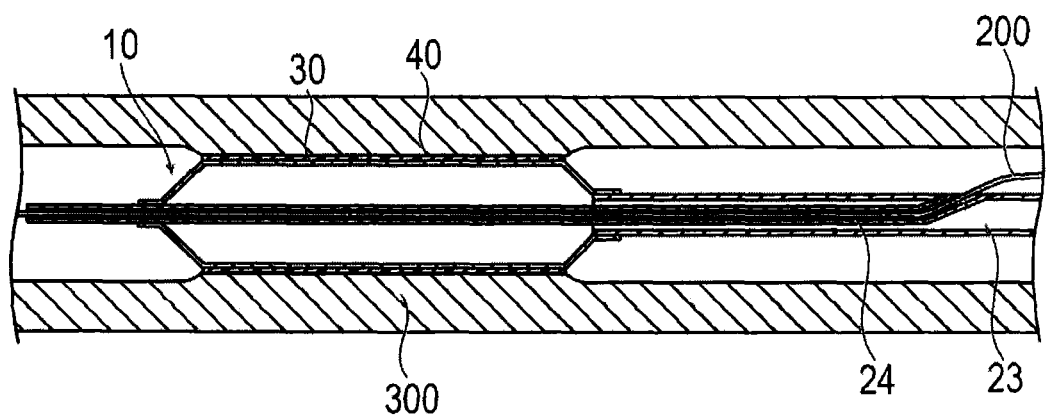
FIG. 19 is a sectional view depicting a state in which a stenosed part of a blood vessel is pushed wide open by the balloon catheter according to the present embodiment.

After the balloon 30 is disposed at the stenosed part 300, a predetermined quantity of the inflation fluid is injected into the inside of the balloon 30 from the proximal opening portion 27 of the hub 26 through the inflation lumen 23 by use of an indeflator or a syringe. By this, as depicted in FIG. 19, the folded balloon 30 is inflated, and the balloon 30 and the base material 41 are stretched in the circumferential direction (see FIG. 6). As a result, the balloon deformed portions 36 and the base material deformed portions 46 are stretched to return into original smooth shapes, and the long axes of the elongate bodies 42 approach perpendicularity to the outer surface of the balloon 30. In addition, the elongate bodies 42 located at the portions of the outer surface of the balloon 30 that overlap with each other at the overlapping portions 35 are relieved from the pressing forces exerted from the overlapping balloon 30; therefore, restoring forces of the balloon deformed portions 36 and the base material deformed portions 46 also act on the elongate bodies 42, so that the long axes of the elongate bodies 42 approach perpendicularity to the outer surface of the balloon 30. Note that part of the elongate bodies 42 may be broken and thereby separated, due to the inflation of the balloon 30. The elongate bodies 42 thus broken become easily movable, so that deliverability of the drug is relatively enhanced. In addition, the inflation of the balloon 30 results in that the stenosed part 300 is pushed wide open (i.e., widened) by the balloon 30. In this instance, the coating layer 40 provided on the outer surface of the balloon 30 and including the drug crystals makes contact with the stenosed part 300. The elongate bodies 42 which are drug crystals included in the coating layer 40 have long axes nearly perpendicular to the outer surface of the balloon 30, and, therefore, they are liable (i.e., likely) to pierce the living body tissue. For this reason, the drug is effectively delivered from the outer surface of the balloon 30 to the stenosed part 300. Consequently, restenosis at the stenosed part 300 is restrained effectively.

When the balloon 30 is inflated to press the coating layer 40 against the living body tissue, the base material 41 which is the water-soluble low-molecular compound included in the coating layer 40 is dissolved gradually or rapidly, and during when the dissolution proceeds, the drug is delivered to the living body. The elongate bodies 42a, 42b and 42c which are crystals of the drug are different in the position of their base portions 45 relative to the base material 41, and, therefore, they differ in deliverability to the living body tissue, as the base material 41 is dissolved gradually or rapidly. In addition, the inflation of the balloon 30 causes the base material 41 to be cracked and become easily soluble, so that the elongate bodies 42 which are the drug crystals become easily releasable from the base material 41. For this reason, by controlling the positions of the base portions 45 of the elongate bodies 42 so as to provide the elongate bodies 42a, 42b and 42c that are different in dissolution property, it is possible to set the deliverability of the drug.

Thereafter, the inflation fluid is sucked and discharged through the proximal opening portion 27 of the hub 26, whereby the balloon 30 is deflated and put into the folded state. Thereafter, the guide wire 200 and the balloon catheter 10 are withdrawn from the blood vessel through the introducer, to finish the procedure.

As has been described above, the balloon catheter 10 according to the present embodiment is a balloon catheter 10 provided on an outer surface of a balloon 30 with a plurality of elongate bodies 42 which are independent crystals of a water-insoluble drug that extend in an elongate form. The elongate bodies 42 have long axes extending in a direction along the outer surface of the balloon 30 when the balloon 30 is in a deflated state, and deformation, when the balloon 30 is inflated from the deflated state, of portions (the balloon 30 or a base material 41) on an outer surface side of the balloon 30 to which end portions of the elongate bodies 42 are fixed causes a force to act on the elongate bodies 42 such that the long axes of the elongate bodies 42 approach perpendicularity to the outer surface of the balloon 30. In the balloon catheter 10 configured in this way, inflation of the balloon 30 causes the long axes of the elongate bodies 42 to approach perpendicularity to the outer surface of the balloon 30, so that the elongate bodies 42 become liable (or likely) to pierce living body tissue, which results in that releasing property of the drug from the outer surface of the balloon 30 and transferability of the drug to the living body tissue can be enhanced, and the drug can be effectively delivered to the living body tissue.

In addition, until the balloon 30 is inflated, the elongate bodies 42 are maintained in the state of extending along the outer surface of the balloon 30, so that the drug crystals can be restrained from peeling off the outer surface of the balloon 30 due to frictional force or flowing out due to blood stream during when the balloon 30 is carried within a blood vessel. In addition, crystals formed in the manner of lying flat on the outer surface of the balloon 30 from the beginning are firmly attached (fixed) to the outer surface of the balloon 30 and/or the adjacent crystal particles. In the present embodiment, on the other hand, the crystal particles standing on the outer surface of the balloon 30 are utilized and are laid flat along the outer surface of the balloon 30. Therefore, the elongate bodies 42 are not formed to be physically fixed to the outer surface of the balloon 30 or the adjacent crystal particles, notwithstanding they extend along the outer surface of the balloon 30. For this reason, while the elongate bodies 42 being small in crystal unit size and high in transferability to the living body tissue can be maintained in the state of lying flat on the outer surface of the balloon 30 until the balloon 30 is inflated, inflation of the balloon 30 can cause the elongate bodies 42 to stand such as to approach perpendicularity to the outer surface of the balloon 30.

In addition, the balloon 30 has the overlapping portions 35 where portions of the outer surface of the balloon 30 overlap with each other when the balloon 30 is folded in the deflated state, and the elongate bodies 42 are provided on the portions of the outer surface of the balloon 30 that overlap with each other at the overlapping portions 35. As a result, the elongate bodies 42 are not exposed to the outside in the deflated state of the balloon 30, so that the elongate bodies 42 can be protected until the balloon 30 is delivered to the target position. Therefore, the drug can be restrained from peeling off the outer surface of the balloon 30 or flowing out into blood stream during delivery, and the drug can be effectively delivered to the living body tissue.

In addition, the water-insoluble drug may be rapamycin, paclitaxel, docetaxel, or everolimus, which helps ensure that restenosis at a stenosed part in a blood vessel can be favorably restrained (or prevented) by the elongate bodies 42.

In addition, the method of manufacturing the balloon catheter 10 according to the present embodiment is a method of manufacturing a balloon catheter 10 provided on an outer surface of a balloon 30 with a plurality of elongate bodies 42 which are crystals of a water-insoluble drug that extend while having independent long axes, the method including: a step of forming the elongate bodies 42 on the outer surface of the balloon 30; a step of forming the balloon 30 with a wing portion 32 projecting in a radial direction; and a step of folding the wing portion 32, formed in the balloon 30, along a circumferential direction. In at least one of the step of forming the wing portion 32 and the step of folding the wing portion 32, portions on an outer surface side of the balloon 30 to which end portions of the elongate bodies 42 are fixed are deformed by a force exerted for deforming the balloon 30, whereby the long axes of the elongate bodies 42 are inclined into a direction along the outer surface of the balloon 30. According to the method of manufacturing the balloon catheter 10, the elongate bodies 42 fixed to the portions on the outer surface side of the balloon 30 can be efficiently inclined by utilizing the force exerted on the balloon 30 in the step of forming the balloon 30 with the wing portion 32 or the step of folding the wing portion 32.

In addition, in the step of folding the wing portion 32, the overlapping portions 35 where portions of the outer surface of the balloon 30 face each other and overlap with each other may be formed, and the long axes of the elongate bodies 42 provided on the portions of the outer surface that face each other at the overlapping portions 35 may be inclined into a direction along the outer surface of the balloon 30, which results in that the force exerted on the balloon 30 for folding the wing portion 32 acts on the overlapping portions 35 indirectly, so that the force acting on the elongate bodies 42 can be controlled, and a desirable force for inclining the elongate bodies 42 can be easily exerted. In other words, the outer surface of the balloon 30 where the overlapping portions 35 are located can take not only a state in which an external force acts but also a state in which an external force hardly acts. For this reason, the elongate bodies 42 standing such as to approach perpendicularity to the outer surface of the balloon 30 can be efficiently formed by inflation of the balloon 30.

In addition, the present disclosure also includes a treatment (therapeutic) method of delivering a drug to a lesion affected area in a body lumen by use of the aforementioned balloon catheter 10. The treatment method includes: a step of inserting the balloon 30 into the body lumen to deliver the balloon 30 to the lesion affected area; a step of inflating the balloon 30 to cause the elongate bodies 42 to be erected at such an angle as to approach perpendicularity to the outer surface of the balloon 30; a step of pressing the erected elongate bodies 42 against living body tissue; and a step of deflating the balloon 30 and withdrawing the balloon 30 out of the body lumen. According to the treatment method configured in this way, the inflation of the balloon 30 causes the long axes of the elongate bodies 42 which are crystals of a water-insoluble drug to approach perpendicularity to the outer surface of the balloon 30, so that the elongate bodies 42 become liable to pierce the living body tissue. As a result, releasing property of the drug from the outer surface of the balloon 30 and transferability of the drug to the living body tissue can be enhanced, and the drug can be effectively delivered to the living body tissue.

Note that the present disclosure is not limited only to the aforementioned embodiment, and various modifications can be made by those skilled in the art within the technical thought of the disclosure. For example, while the balloon catheter 10 according to the above embodiment is of the rapid exchange type, the balloon catheter may be of the over-the-wire type.

In addition, while the long axes of the elongate bodies 42 formed on the outer surface of the balloon 30 are inclined in the process of folding of the balloon 30 in the present embodiment, the elongate bodies 42 may be inclined relative to the outer surface of the balloon 30 by pressing by the blades 122 in the process of pleating (see FIG. 15).

Figure 20:
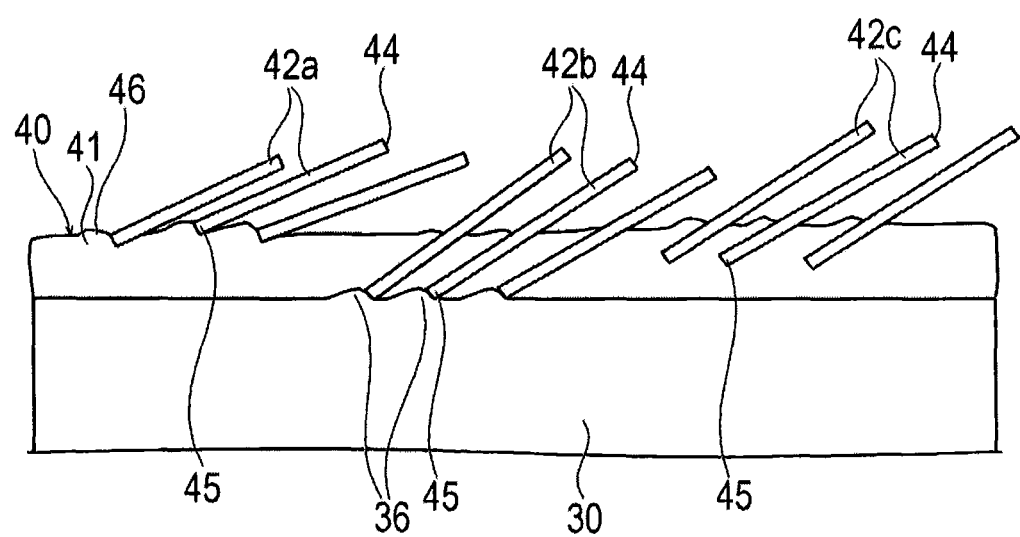
FIG. 20 is a schematic view of elongate bodes and a base material in a case where the base material is in a film-shaped amorphous state.
Figure 22:
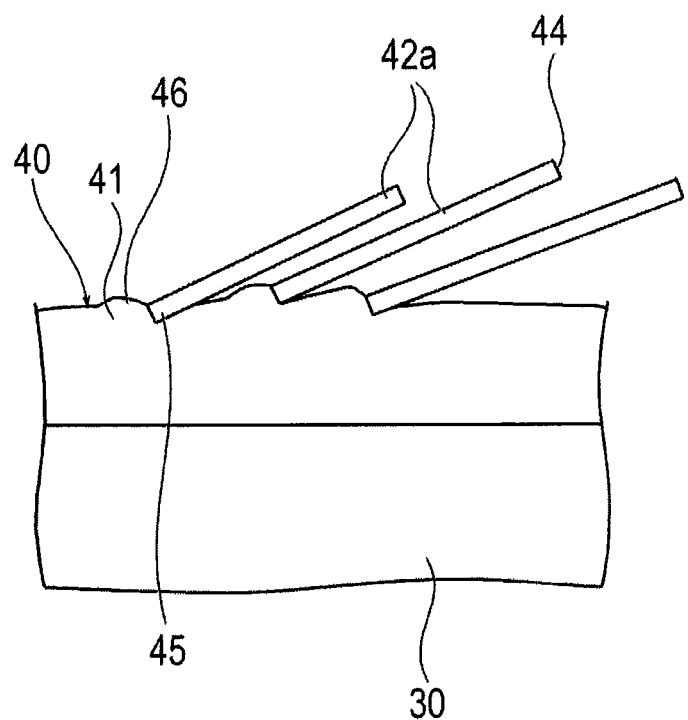
FIG. 22 is a schematic view of first elongate bodies and the base material, on an outer surface of a balloon.
Figure 23:
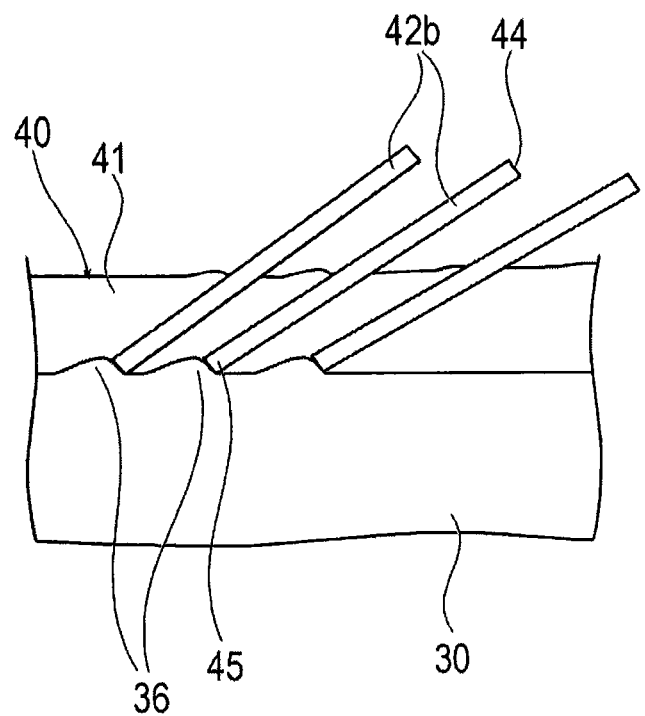
FIG. 23 is a schematic view of second elongate bodies and the base material, on the outer surface of the balloon.
Figure 24:
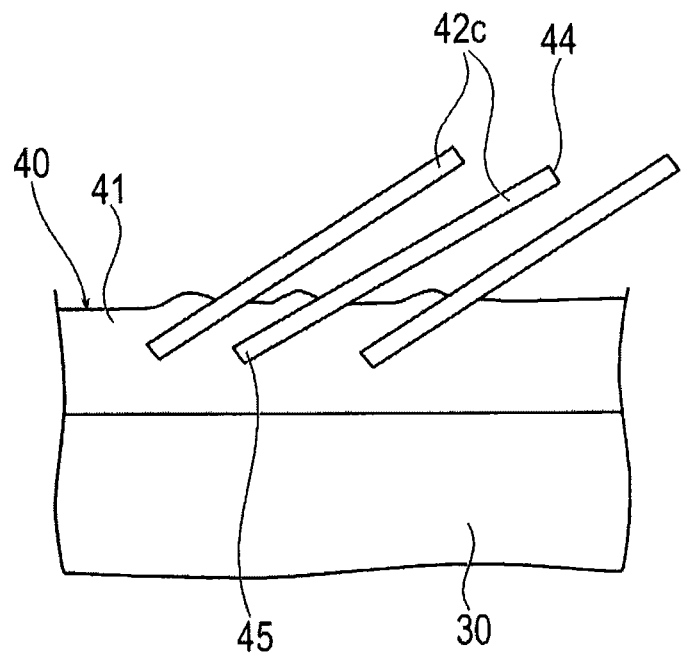
FIG. 24 is a schematic view of third elongate bodies and the base material, on the outer surface of the balloon.

As aforementioned, the base material 41 is present as an amorphous phase, crystal particles, or a mixture of the amorphous phase and the crystal particles. While the base material 41 in FIG. 4 is in a state of crystal particles and/or a particulate amorphous phase, the base material 41 may be in a film-shaped amorphous state, as depicted in FIG. 20. As depicted in FIG. 22, first elongate bodies 42a extend from the outer surface of the base material 41 toward the outside of the surface. As depicted in FIG. 23, second elongate bodies 42b extend from the outer surface of the balloon 30 to the outside of the base material 41 by penetrating the base material 41. As depicted in FIG. 24, third elongate bodies 42c extend from the inside of the base material 41 to the outside of the base material 41.

Figure 21A:
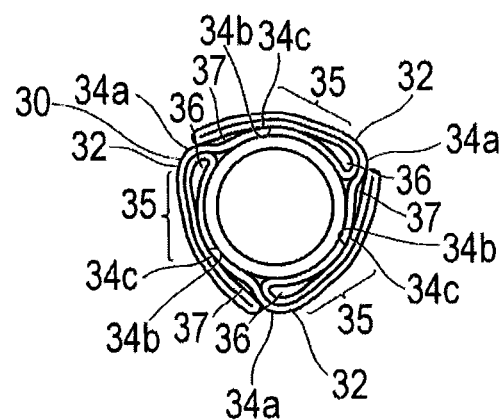
FIGS. 21A and 21B are sectional views of balloons in a folded state that have wing portions in different forms.

In addition, while a tip end of the wing portion 32 of the folded balloon 30 does not reach the adjacent wing portion 32 in the present embodiment, the tip end of the wing portion 32 may reach the adjacent wing portion 32, as in two examples depicted in FIG. 21. In the example of FIG. 21A, a root-side space portion 36 is formed between the root side of the wing portion 32 and the intermediate portion 34c, and a tip-side space portion 37 is formed between the tip side of the wing portion 32 and the intermediate portion 34c. In this case, in those regions of the wing inner portions 34b and the intermediate portions 34c which face the root-side space portion 36 and the tip-side space portion 37, namely, in the regions where the wing inner portion 34b and the intermediate portion 34c do not make close contact with each other, the elongate bodies 42 hardly receive pressing forces. In the regions where the wing inner portion 34b and the intermediate portion 34c do not make close contact with each other, therefore, the elongate bodies 42 are hardly inclined, and desirable base material deformed portions 46 and desirable balloon deformed portions 36 are hardly formed. In addition, in those regions of the wing inner portions 34b and the intermediate portions 34c which do not face the root-side space portion 36 or the tip-side space portion 37, namely, in the regions where the wing inner portion 34b and the intermediate portion 34c are in close contact with each other, the elongate bodies 42 are liable to receive pressing forces. In these regions, therefore, the elongate bodies 42 are liable to be inclined, and desirable base material deformed portions 46 and desirable balloon deformed portions 36 are liable to be formed.

Figure 21B:
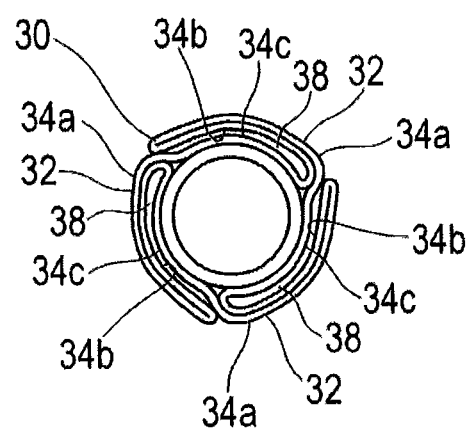

In the example of FIG. 21B, a space portion 38 is formed between wing portion 32 and the intermediate portion 34c, throughout the region ranging from the root side of the wing portion 32 to the adjacent wing portion 32. In this case, the elongate bodies 42 hardly receive pressing forces, in the whole of the regions of the wing inner portion 34b and the intermediate portion 34c which face each other. In the regions where the wing inner portion 34b and the intermediate portion 34c which face each other, therefore, the elongate bodies 42 are hardly inclined, and desirable base material deformed portions 46 and desirable balloon deformed portions 36 are hardly formed.

In addition, the balloon folding apparatus 100 also may not be used for folding the balloon 30.

In addition, the base material which is the excipient may not be provided in the coating layer on the outer surface of the balloon 30.

Figure 25:
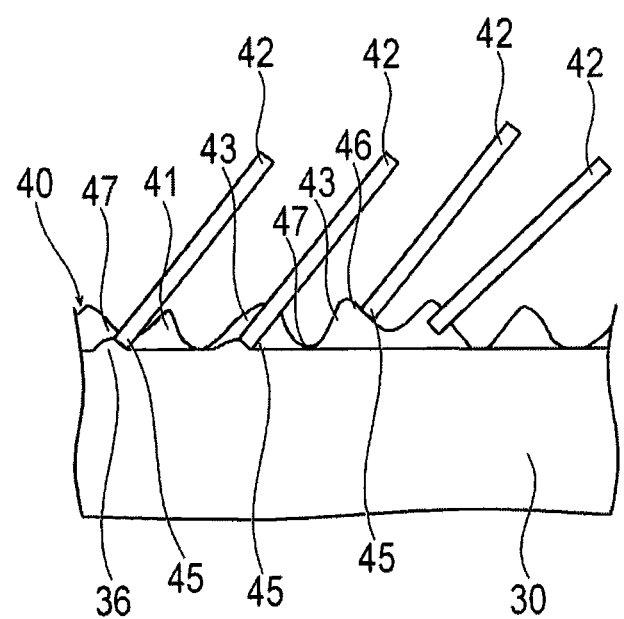
FIG. 25 is a schematic view of the elongate bodies and the base material, on the outer surface of the balloon.

In addition, as depicted in FIG. 25, the base material 41 which is an additive layer may have projections and recesses (ruggedness). The height of the projections is 0.1 μm to 5 μm. The elongate bodies 42 which are crystals are projecting from projecting portions 43 that constitute the projections of the base material 41. In other words, the elongate bodies 42 which are crystals are supported by the projecting portions 43 of the base material 41. Note that the base material 41 may have the projecting portions 43 from which the elongate bodies 42 are not projecting. The elongate bodies 42 which are crystals may project from recessed portions 47 that constitute the recesses of the base material 41. The base material 41 may have both the projecting portions 43 which support the elongate bodies 42 and the projecting portions 43 which do not support the elongate bodies 42. The base material 41 may have both the recessed portions 47 which support the elongate bodies 42 and the recessed portions 47 which do not support the elongate bodies 42. In addition, the base material 41 may have both the projecting portions 43 which support the elongate bodies 42 and the recessed portions 47 which support the elongate bodies 42. The base material 41 may have both the elongate bodies 42 which are substantially perpendicular to the outer surface of the balloon 30 and the elongate bodies 42 which are inclined relative to the outer surface of the balloon 30. The base portions 45 of the elongate bodies 42 may be in direct contact with the outer surface of the balloon 30. Alternatively, the base portions 45 of the elongate bodies 42 may be located in the inside of the base material 41, without making contact with the outer surface of the balloon 30. The base material 41 may have both the elongate bodies 42 which are in direct contact with the outer surface of the balloon 30 and the elongate bodies 42 which are not in contact with the outer surface of the balloon 30.

Figure 26:
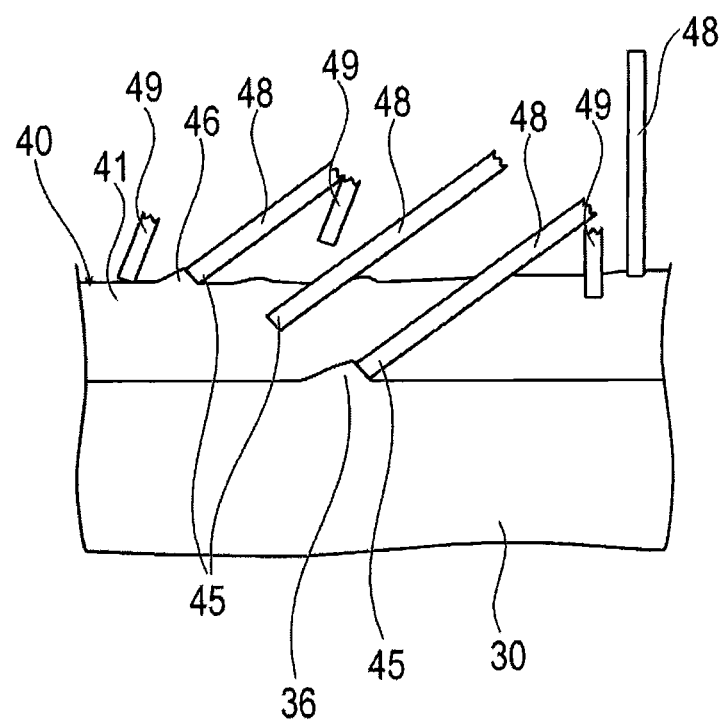
FIG. 26 is a schematic view of fixed-side elongate bodies, separate-side elongate bodies and the base material, on the outer surface of the balloon.

In addition, as depicted in FIG. 26, the crystals may include fixed-side elongate bodies 48 (balloon base material contact crystal particles) originally projecting from the base material 41, and separate-side elongate bodies 49 (balloon base material non-contact crystal particles) separated from the fixed-side elongate bodies 48. The amount of the fixed-side elongate bodies 48 is larger than that of the separate-side elongate bodies 49. The separate-side elongate bodies 49 are formed by breaking of elongate crystals and separation from the fixed-side elongate bodies 48 when the balloon 30 is folded in the manner of winding around the inner tube 22. At least part of a distal portion, a proximal portion, and a portion between the distal portion and the proximal portion, of the separate-side elongate body 49, is in contact with the base material 41. Part of the separate-side elongate body 49 may be embedded in the base material 41. The presence of the base material 41 helps ensure that the fixed-side elongate bodies 48 and the separate-side elongate bodies 49 are not liable to fall off (i.e., be removed from) the balloon 30 during carrying, because of their interactions with the base material 41. The fixed-side elongate bodies 48 and the separate-side elongate bodies 49 become liable to be released through dissolution of the base material 41 upon contact with water (blood) when the balloon 30 is inflated. The fixed-side elongate bodies 48 and the separate-side elongate bodies 49 differing in morphological form are different in releasing property, which is preferable from the viewpoint of their action on the living body. The fixed-side elongate bodies 48 may be formed through breaking of crystals, or may be formed without breaking of crystals. The base material 41 may include both the fixed-side elongate bodies 48 formed through breaking of crystals, and the fixed-side elongate bodies 48 formed without breaking of crystals. The fixed-side elongate bodies 48 may be standing from the base material 41, or may be lying flat along the base material 41. The base material 41 may have both the fixed-side elongate bodies 48 standing from the base material 41, and the fixed-side elongate bodies 48 lying flat along the base material 41.

The length of the crystals fixed to the base material 41, before breaking of the crystals fixed to the base material 41, is 5 μm to 20 μm, for example. The length of the broken crystals is, for example, 3 μm to 20 μm. The length of the fixed-side elongate bodies 48 formed through breaking is, for example, 5 μm to 20 μm. The length of the separate-side elongate bodies 49 is, for example, 3 μm to 10 μm.

The detailed description above describes a balloon catheter having a balloon coated on its surface with a drug, a method of manufacturing the balloon catheter, and a treatment method. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A balloon catheter, the balloon catheter comprising:
an outer surface of a balloon with a plurality of elongated bodies, the outer surface of the balloon being smooth and non-porous and the plurality of elongated bodies being crystals of a water-insoluble drug, each of the plurality of elongated bodies having an independent longitudinal axis and extending in a direction away from the outer surface of the balloon, and the independent longitudinal axes of each of the plurality of elongated bodies is inclined relative to the outer surface of the balloon and extending in directions along the outer surface of the balloon when the balloon is in a deflated state;
a base material, the base material being an additive layer containing a water-soluble low-molecular compound disposed on the outer surface of the balloon, and wherein the plurality of elongated bodies comprise:
first elongated bodies originating on an outer surface of the base material and extending in the direction away from the outer surface of the balloon, the first elongated bodies terminating outside of the base material;
second elongated bodies originating on the outer surface of the balloon and extending to an outside of the base material by penetrating the base material, the second elongated bodies terminating outside of the base material; and
third elongated bodies originating from an inside of the base material and extending to the outside of the base material, the third elongated bodies terminating outside of the base material; and
when the balloon is inflated from the deflated state, deformation of portions on an outer surface side of the balloon to which end portions of the plurality of elongated bodies are fixed causes a force to act on the plurality of elongated bodies such that the independent longitudinal axes of the plurality of elongated bodies change direction relative to the outer surface of the balloon on which the plurality of elongated bodies are arranged and approach perpendicularity to the outer surface of the balloon.

2. The balloon catheter according to claim 1, wherein the balloon has an overlapping portion where portions of the outer surface of the balloon overlap with each other when the balloon is folded in the deflated state; and
the plurality of elongated bodies being provided on the portions of the outer surface of the balloon that overlap with each other at the overlapping portion.

3. The balloon catheter according to claim 1, wherein the water-insoluble drug is rapamycin, paclitaxel, docetaxel, or everolimus.

4. The balloon catheter according to claim 1, wherein an inclination angle of the long axes of the plurality of elongated bodies relative to the outer surface of the balloon after the inflation of the balloon is greater than an inclination angle of the long axes of the plurality of elongated bodies in the deflated state.

5. The balloon catheter according to claim 4, wherein the inclination angle of the long axes of the plurality of elongated bodies relative to the outer surface of the balloon after the inflation of the balloon is 60 degrees to 90 degrees.

6. The balloon catheter according to claim 1, wherein the plurality of elongated bodies each include a base end, a tip end and a side surface, the base end of each of the plurality of elongated bodies being in direct contact with the outer surface of the balloon or in contact with the base material on the outer surface of the balloon.

7. The balloon catheter according to claim 6, wherein the plurality of elongated bodies include solid elongated bodies and hollow elongated bodies, the hollow elongated bodies including at least a portion near the tip end that is hollow.

8. The balloon catheter according to claim 1, wherein the plurality of elongated bodes are substantially rectilinear in a long axis direction.

9. The balloon catheter according to claim 1, wherein the plurality of elongated bodes each has a length of 5 µm to 20 µm, and wherein each of the plurality of elongated bodies stand independently, without making contact with one another.

10. The balloon catheter according to claim 1, wherein the water-soluble low-molecular compound of the base material is crystal particles.

11. The balloon catheter according to claim 1, wherein all of the elongated bodies make up at least 50% of a total amount of drug crystals on the outer surface of the balloon based on a total volume of the drug crystals on the outer surface of the balloon.

12. A treatment method of delivering a drug to a lesion affected area in a body lumen by use of a balloon catheter, the balloon catheter having an outer surface of a balloon with a plurality of elongated bodies, the outer surface of the balloon being smooth and non-porous and the plurality of elongated bodies being crystals of a water-insoluble drug, each of the plurality of elongated bodies having an independent longitudinal axis and extending in a direction away from the outer surface of the balloon, and the independent longitudinal axes of each of the plurality of elongated bodies is inclined relative to the outer surface of the balloon and extending in directions along the outer surface of the balloon when the balloon is in a deflated state, and a base material, the base material being an additive layer containing a water-soluble low-molecular compound disposed on the outer surface of the balloon, and wherein the plurality of elongated bodies includes first elongated bodies originating on an outer surface of the base material and extending in the direction away from the outer surface of the balloon, the first elongated bodies terminating outside of the base material, the treatment method comprising:
inserting the balloon into the body lumen to deliver the balloon to the lesion affected area;
inflating the balloon to cause the plurality of elongated bodies to change direction relative to the outer surface of the balloon on which the plurality of elongated bodies are arranged and to be erected at such an angle as to approach perpendicularity to the outer surface of the balloon; and
pressing the erected elongated bodies against living body tissue.

13. The treatment method according to claim 12, further comprising:
deflating the balloon and withdrawing the balloon out of the body lumen.

14. The treatment method according to claim 12, wherein the plurality of elongated bodies are formed in an overlapping portion where portions of the outer surface of the balloon face each other and overlap with each other to provide a wing portion, the method further comprising:
folding the wing portion, in which the independent longitudinal axes of the plurality of elongated bodies provided on the portions of the outer surface that face each other at the overlapping portion are inclined into directions along the outer surface of the balloon.

15. The treatment method according to claim 12, wherein the water-insoluble drug is rapamycin, paclitaxel, docetaxel, or everolimus.

16. The treatment method according to claim 12, wherein the plurality of elongated bodies further comprises:
second elongated bodies originating on the outer surface of the balloon and extending to the outside of the base material by penetrating the base material, the second elongated bodies terminating outside of the base material; and
third elongated bodies originating from an inside of the base material and extending to the outside of the base material, the third elongated bodies terminating outside of the base material.

17. A balloon catheter, the balloon catheter comprising:
an outer surface of a balloon with a plurality of elongated bodies, the outer surface of the balloon being smooth and non-porous and the plurality of elongated bodies being crystals of a water-insoluble drug, each of the plurality of elongated bodies having an independent longitudinal axis and extending in a direction away from the outer surface of the balloon, and the independent longitudinal axes of each of the plurality of elongated bodies is inclined relative to the outer surface of the balloon and extending in directions along the outer surface of the balloon when the balloon is in a deflated state;
a base material, the base material being an additive layer containing a water-soluble low-molecular compound disposed on the outer surface of the balloon, and wherein the plurality of elongated bodies includes first elongated bodies originating on an outer surface of the base material and extending in the direction away from the outer surface of the balloon, the first elongated bodies terminating outside of the base material; and
when the balloon is inflated from the deflated state, deformation of portions on an outer surface side of the balloon to which end portions of the plurality of elongated bodies are fixed causes a force to act on the plurality of elongated bodies such that the independent longitudinal axes of the plurality of elongated bodies change direction relative to the outer surface of the balloon on which the plurality of elongated bodies are arranged and approach perpendicularity to the outer surface of the balloon.

* * * * *